(12) United States Patent
Niedospial, Jr.

(10) Patent No.: US 6,179,823 B1
(45) Date of Patent: Jan. 30, 2001

(54) MULTIPLE USE UNIVERSAL CONNECTOR FLEXIBLE MEDICAL CONTAINER ASSEMBLY

(75) Inventor: John J. Niedospial, Jr., Burlington, NJ (US)

(73) Assignee: Bracco Research USA, Princeton, NJ (US)

( * ) Notice: Under 35 U.S.C. 154(b), the term of this patent shall be extended for 0 days.

(21) Appl. No.: 09/246,153

(22) Filed: Feb. 8, 1999

Related U.S. Application Data

(63) Continuation-in-part of application No. 09/009,487, filed on Jan. 20, 1998, now Pat. No. 6,019,751.

(51) Int. Cl.[7] .......................... A61B 19/00; A61B 17/06; B65D 39/00
(52) U.S. Cl. .......................... 604/408; 604/415; 215/247; 215/249; 206/438; 206/828
(58) Field of Search ................................... 604/403, 408, 604/411–415, 905; 215/247, 249; 206/828, 438

(56) References Cited

U.S. PATENT DOCUMENTS

| Re. 32,065 | 1/1986 | Ralston et al. . |
|---|---|---|
| 2,619,277 | 11/1952 | Shumann . |
| 4,088,166 | 5/1978 | Miller . |
| 4,150,744 | 4/1979 | Fennimore . |
| 4,509,197 | 4/1985 | Long . |
| 4,548,605 | 10/1985 | Iwamoto et al. . |
| 4,660,721 | 4/1987 | Mykleby . |
| 4,872,553 | 10/1989 | Suzuki et al. . |
| 4,892,537 | 1/1990 | Carmen et al. . |
| 4,976,707 | 12/1990 | Bodicky et al. . |
| 5,071,413 | 12/1991 | Utterberg . |
| 5,086,915 | 2/1992 | Yashima et al. . |
| 5,088,994 | 2/1992 | Porat . |
| 5,360,413 | 11/1994 | Leason et al. . |
| 5,391,150 | 2/1995 | Richmond . |
| 5,423,794 | 6/1995 | Adolf et al. . |
| 5,540,674 | * 7/1996 | Karas et al. .......................... 604/415 |
| 5,573,516 | 11/1996 | Tyner . |
| 5,728,086 | * 3/1998 | Niedospial, Jr. ...................... 604/408 |
| 5,728,087 | 3/1998 | Niedospial, Jr. . |
| 5,738,671 | * 4/1998 | Niedospial, Jr. et al. ........... 604/408 |
| 5,779,693 | * 7/1998 | Ropiak et al. ....................... 604/408 |
| 5,817,082 | * 10/1998 | Niedsopial, Jr. et al. ........... 604/414 |
| 5,902,298 | * 5/1999 | Niedospial, Jr. et al. .......... 604/414 |
| 5,941,866 | * 8/1999 | Niedospial, Jr. ..................... 604/408 |
| 5,984,912 | * 11/1999 | Niedospial, Jr. et al. .......... 604/408 |
| 6,019,751 | * 2/2000 | Gabbard et al. ..................... 604/408 |

* cited by examiner

Primary Examiner—Dennis Ruhl
(74) Attorney, Agent, or Firm—Imre Balogh

(57) ABSTRACT

Multiple use universal connector designed for use in various containers having a fluid port for accessing to the content of the container or for transferring fluid into the container. The multiple use universal connector incorporates a diaphragm capable of being penetrated repeatedly by an access means such as a luer connector or a syringe having a sharp or blunt cannula for fluid communication between the content of the container and the access means. The multiple use universal connector re-seals itself after being penetrated and the access means removed therefrom.

51 Claims, 33 Drawing Sheets

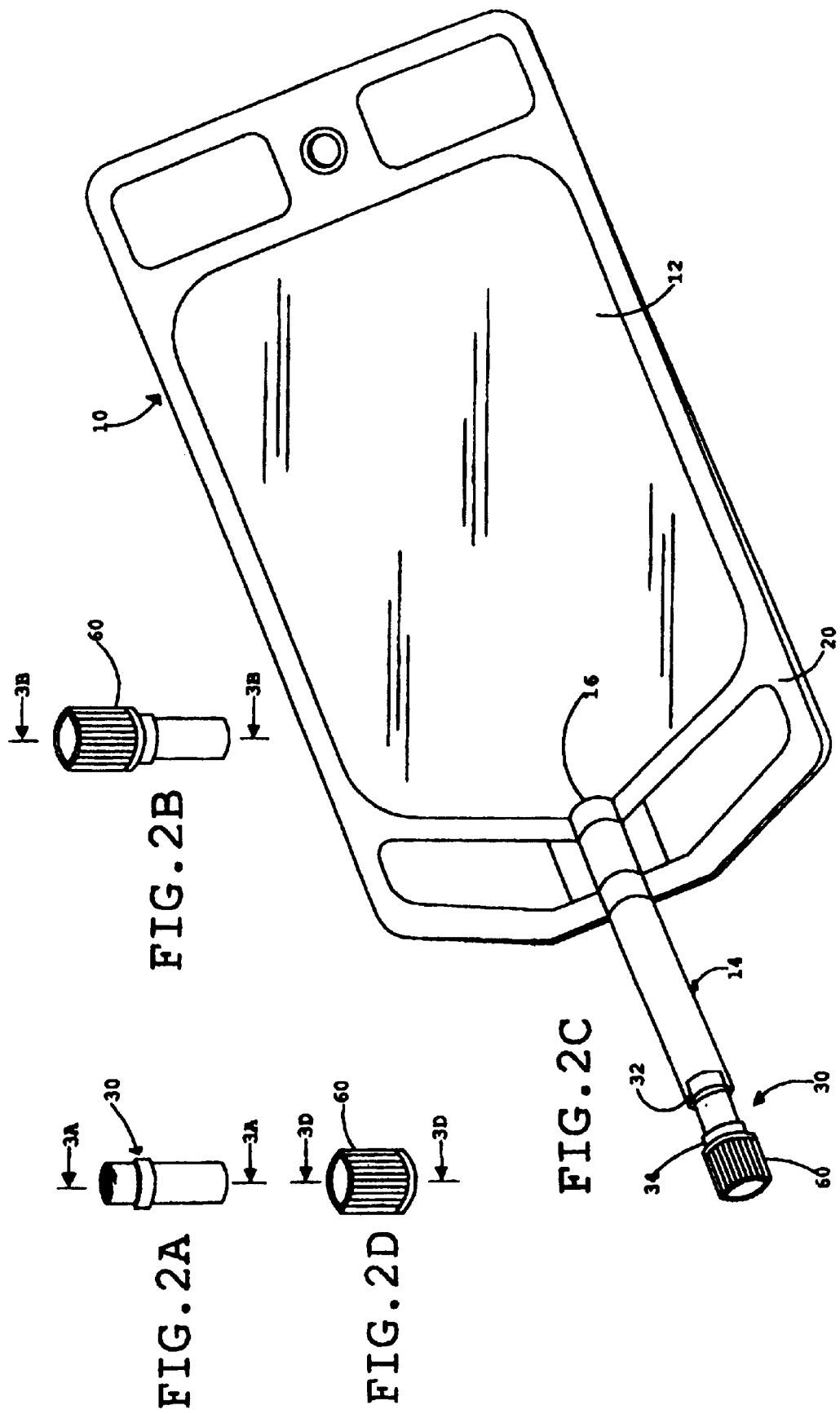

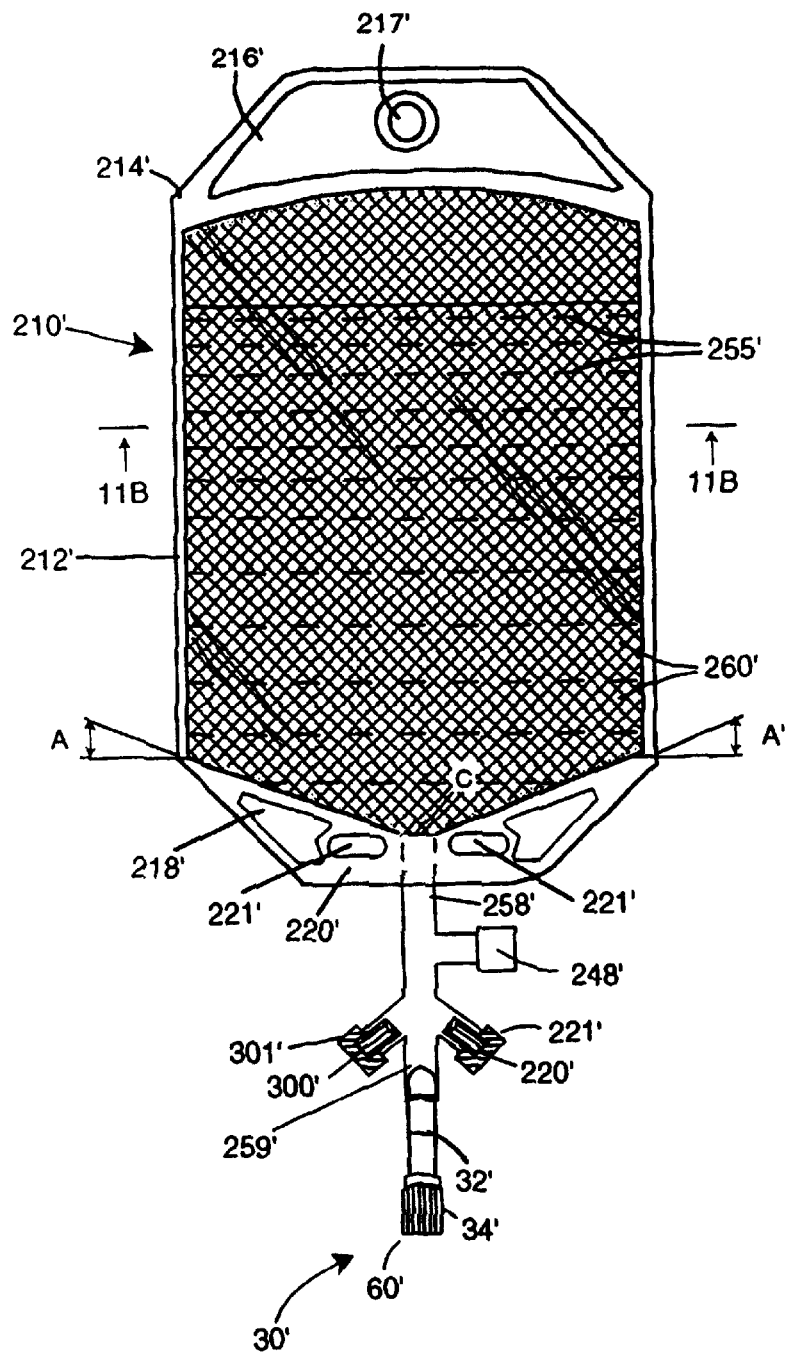
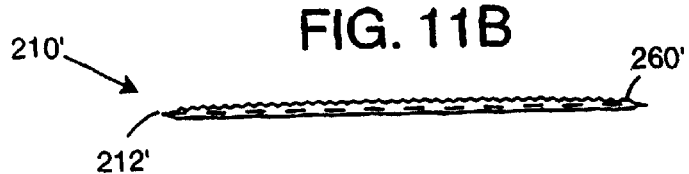

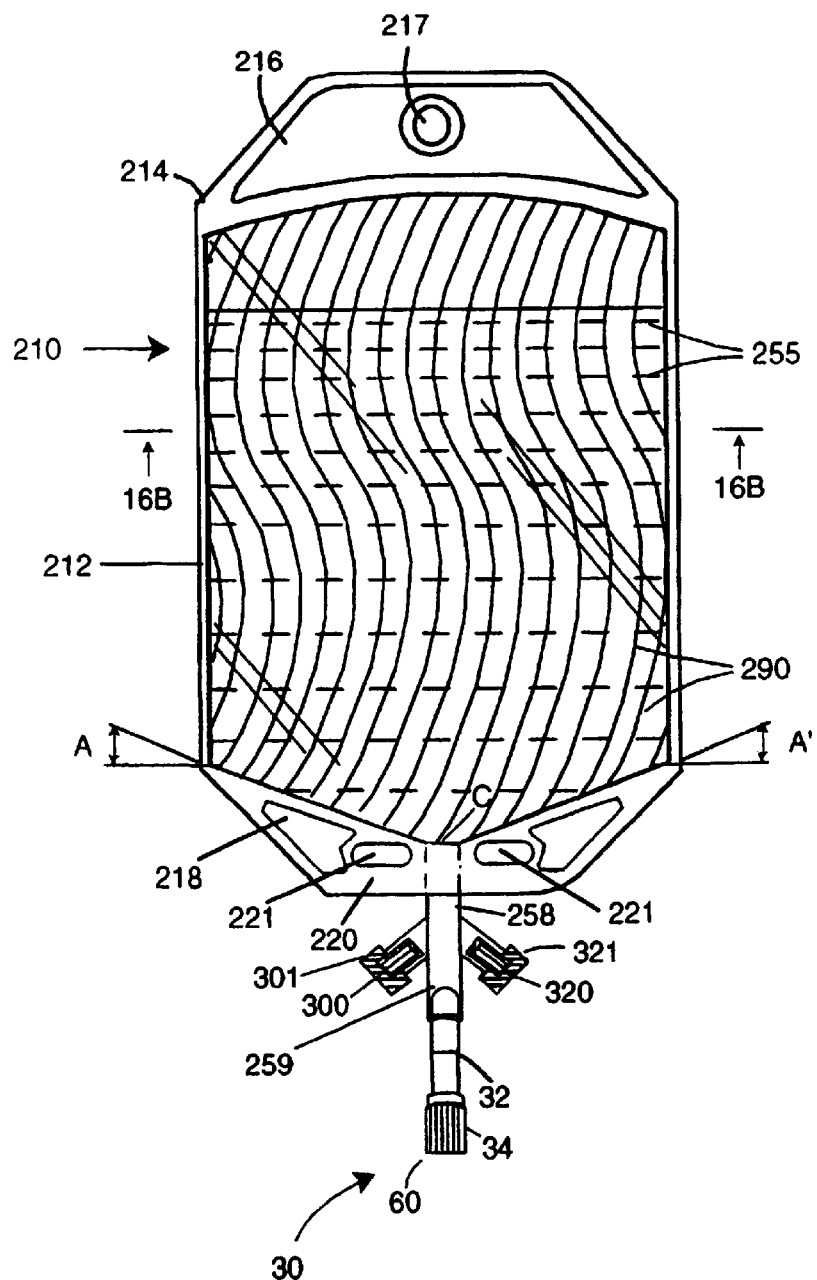
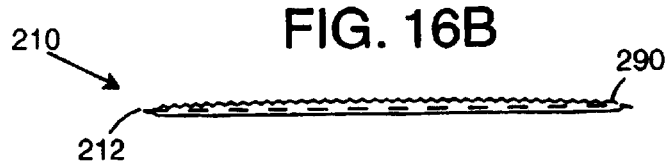

MULTIPLE USE UNIVERSAL CONNECTOR FLEXIBLE MEDICAL CONTAINER ASSEMBLY

This application is a continuation-in-part of application Ser. No. 09/009,487, filed on Jan. 20, 1998 now U.S. Pat. No. 6,019,751.

BACKGROUND OF THE INVENTION

1. Field of the Invention

This invention relates to a universal connector connectable to containers having fluid contents therein designed for delivery to a site of administration. More particularly, the invention relates to a universal connector having a self-sealing means so that a pharmaceutical fluid contained in a container closed by the universal connector can be repeatedly accessed.

2. Reported Developments

Parenteral fluids, such as therapeutic drugs, diagnostic contrast media and nutrients are conventionally administered to a patient from a container, such as a collapsible bag or bottle having a fluid exit port. The fluid exit port may include means, such as a tube, spike or cannula, the distal end of which is in communication with the fluid content of the container and the proximal end of which is connected to the desired site on the patient. Conventionally, the proximal end of said means includes a needle that can puncture the patient. The fluid exit port is sealed by a membrane which is punctured by inserting a spike into the exit port when fluid delivery is desired.

One approach used by the prior art to penetrate the membrane covering the fluid exit port comprises the use of syringes or spikes which carry the danger of accidental injuries caused by the sharp points of the needles and spikes. Such injuries accidentally inflicted on the health practitioner carry the further risk of getting infected with diseases such as AIDS. In order to reduce the danger of accidental injuries, spikes having relatively blunt tips were used. However, such spikes puncture a large area of the membrane and once the spikes are removed the membrane no longer seals the fluid exit port.

Another approach used by the prior art is the provision of a tubular member which is more blunt than a spike so that it is unlikely to penetrate the skin yet capable of penetrating the latex diaphragm type seals.

Still another approach used by the prior art is a valve positioned in the fluid exit port, the valve being operable by engagement with a spikeless or needleless IV component and contains a resilient valve disc positioned in the fluid passageway and blocks fluid flow when the disc is in the closed position, and allows fluid flow when the disc is in the open position.

Still another needleless connector of the prior art uses a resilient conical valve head in a housing. The conical valve head is positioned against the valve seat to form a seal. When the male fitting of a syringe, or some other device, is inserted into the inlet of the housing, it pushes the tip portion of the resilient valve head inwardly so that the valve head is deformed away from the valve seat thereby allowing fluid communication. In still other embodiments of the prior art, a needleless connector includes an elastomeric conical valve head biased against a conical valve seat by a helical spring to form a seal.

The above generally described devices have greatly reduced the needle-stick injuries associated with the use of syringes. The devices also advanced the prior art by providing convenient connectors which can be easily connected to the containers of medical fluids.

However, there still exists the need to provide a universal connector which may be used with a wide variety of connection sites. A seal or diaphragm is a main component of the herein-described invention which does not require penetration by any sharp or even blunt object in order to establish fluid communication between the content of the container and the site of delivery. The seal or diaphragm serves as access means and provides for hermetic sealing, safe handling, sterilization and storing. The seal or diaphragm is designed for multiple use so that the medical fluid can be accessed repeatedly. After each withdrawal of the desired amount of the medical fluid, the seal or diaphragm self-seals itself thereby preventing contamination of the medical fluid by air-born particles such as dust and bacteria.

SUMMARY OF THE INVENTION

In accordance with the present invention there is provided a multiple use universal connector which can be used to repeatedly access the fluid content of a container or to repeatedly transfer a fluid into the container. The multiple use universal connector can be used in collapsible and non-collapsible bags, bottles and vials made of glass or polymeric material which contain a fluid exit port into which the universal connector is inserted sealing the fluid exit port. The fluid contained in the container may be a therapeutic liquid, diagnostic media or a nutritional formula which can be sterilized in bulk and then aseptically transferred into the container or it can be sterilized in the container stoppered with the universal connector. The multiple use universal connector is made of rigid or semi-rigid polymeric materials such as polyvinyl chloride, polyethylene and polypropylene.

The fluid in a container stoppered by the multiple use universal connector can be accessed by means well-known in the art, such as syringes having sharp or blunt needle cannulas. Preferably, the access means comprises a luer connector in order to prevent accidental injuries to health care workers and patients caused by the use of syringes.

The multiple use universal connector comprises:

(1) a connector body of tube-like configuration the distal end of which is designed to be slideably insertable into the fluid exit port, and the proximal end of which is designed to seal the content of the container by an elastomeric membrane and also to receive a removable cap; and (2) a removable cap threaded onto the proximal end of the connector which, prior to use, is removed so that the content of the container could be accessed by the use of a luer connector having a configuration that is similar to the configuration of the cap or by other access means, such as sharp or blunt needle cannulas.

The elastomeric membrane sealing the proximal end of the universal connector is of an inert, gas-impermeable polymeric material capable of flexing under internal or external pressures such as exerted thereon during steam sterilization. It preferably has a thickness of from about 0.001 mm to about 1.00 mm and a durometer of from about 25 to about 80 Shore A. It is capable of being ruptured by the twisting motion of a blunt luer connector or syringes having sharp or blunt needle cannula. The configuration of the elastomeric membrane is M-shaped having vertical leg portions and a top surface resembling a cup shape.

The tube-like body of the universal connector further comprises: first cap-locking ring on the proximal end of the body which serves as a male thread to receive the removable cap; and second cap-locking ring spaced from the first cap-locking ring towards the distal end of the tube-like body, which serves as stopping means for the cap when the cap is threaded onto the tube-like body of the universal connector.

The multiple use universal connector is preferably used in the embodiments disclosed in U.S. Pat. Nos. 5,728,087 and 5,728,086 each of which is incorporated herein by reference in its entirety, denoted as first embodiment and as second embodiment.

In the first embodiment the universal multiple use universal connector and a unitary, flexible container such as a bag, pouch or bottle, for the containment and delivery of parenteral solutions, are combined to provide a delivery system comprising:

(a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferably from 10° to 20° from the center of said bottom portion to direct and facilitate the flow of content of the solution contained in the pouch towards the center of said bottom portion; all or at least portions of said interior of said pouch being mechanically deformed to prevent adhesion of said first and second plastic sheets; and (b) a combination access member of inverted Y shape configuration having:

(b1) a stem with a proximal end and a distal end, said proximal end located at the bottom, center portion of the pouch sealed between the two sheets in the periphery thereof; and (b2) a pair of tines having proximal and distal ends, the proximal ends thereof being integral with the stem of the access member; the combination access member comprising:

(1) an IV access port equipped with the multiple use universal connector;

(2) a needle access port located in one of the tines of the combination access member; and (3) a spike access port located in the other of the tines of the combination access member;

said universal connector needle and spike access ports being equipped with caps.

Preferably, the stem of the combination access member is equipped with a vent adjacent to the proximal end thereof This embodiment of the present invention provides:

IV access through the multiple use universal connector, needle access and spike access through the respective needle and spike access ports.

Preferably the top portion at the periphery of the pouch comprises at least one hole for suspending the container when it is in use for delivering the content thereof to the delivery site, and the bottom portion at the periphery of the pouch comprises at least one and preferably a plurality of holes to facilitate suspending the container during the filling process.

In the second embodiment the universal multiple use universal connector and a unitary, flexible plastic container, such as a bag, pouch or bottle for the containment and delivery of parenteral solutions, are combined to provide a delivery system comprising:

a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferable from 10° to 20° from the center of said bottom portion and relative to a horizontal plane crossing the center of said bottom portion to direct and facilitate the flow of content of the solution contained in the pouch towards the center of said bottom portion; all, or at least portions of said interior of said pouch being mechanically deformed to prevent adhesion of said first and second plastic sheets;

b) an IV access port equipped with the multiple use universal connector located in the center bottom portion of the pouch;

c) a needle access port located on one side of the IV access port in the bottom portion of the pouch; and d) a spike access port located on the other side of the IV access port in the bottom portion of the pouch;

said universal connector being equipped with a cap and said needle and spike access ports being equipped with crimp seals.

Preferably the IV access port is equipped with a vent positioned between the multiple use universal connector and the bottom center portion of the pouch.

Preferably the top portion at the periphery of the pouch comprises at least one hole for suspending the container when it is in use for delivering the content thereof to the delivery site and the bottom portion at the periphery of the pouch comprises at least one, and preferably a plurality, of holes to facilitate suspending the container during the filling process.

BRIEF DESCRIPTION OF THE DRAWINGS

In the drawings, like numerals indicate like elements and primes (') indicate counterparts of like elements.

FIG. 2A is a perspective view of the multiple use universal connector of the present invention without the cap attached;

FIG. 2B is a perspective view of the multiple use universal connector of the present invention with the cap attached;

FIG. 2C is a perspective view of the multiple use universal connector of the present invention with the cap attached and connected to the medical bag of FIG. 1;

FIG. 2D is a perspective view of the cap;

FIG. 11A is a plan view of the universal, flexible container multiple use universal connector assembly shown in FIG. 9 one wall of which is embossed in a checkerboard fashion;

FIG. 11B is a cross-section of the universal, flexible container multiple use universal connector assembly shown in FIG. 11A taken along the line 11B—11B;

FIG. 16A is a plan view of the flexible container multiple use universal connector assembly shown in FIG. 8 one wall of which is embossed with vertically oriented S-shape channels;

FIG. 16B is a cross-section of the universal, flexible container multiple use universal connector assembly shown in FIG. 16A taken along the line 16B—16B;

DETAILED DESCRIPTION OF THE INVENTION

Figure 1:
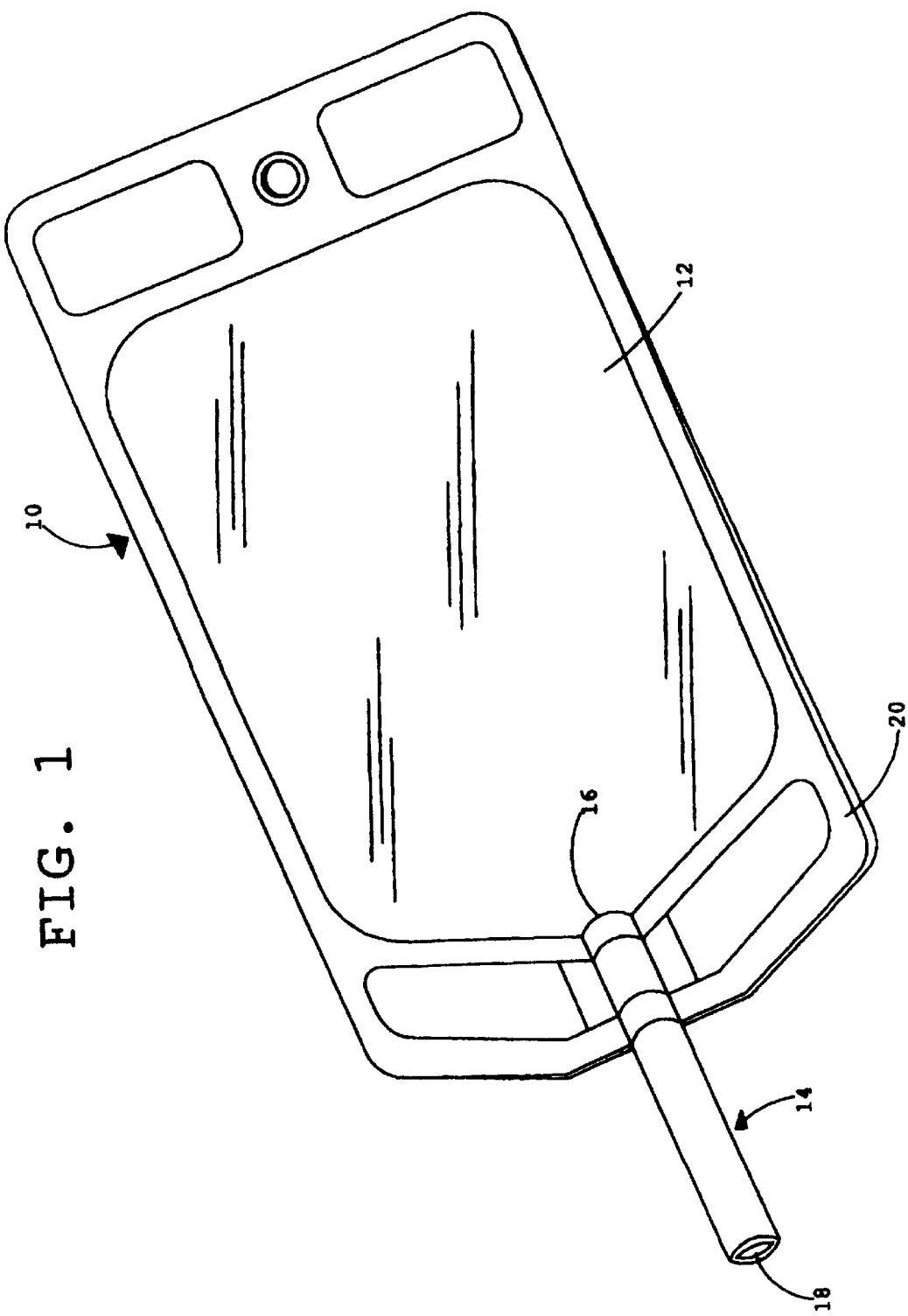
FIG. 1 is a perspective view of a medical bag.

Referring to FIGS. 1, 2A, 2B, 2C and 2D, there is shown an intravenous bag 10 of conventional generally rectangular configuration made of inert, flexible, polymeric material, such as polyvinylchloride. The multiple use universal connector of the present invention will be described in reference to such flexible, polymeric bags, however, the multiple use universal connector can be used with other fluid containers such as bottles and vials of various configurations made of rigid or semi-rigid materials. Such containers will have fluid exit ports into which the universal connector can slideably be attached or it can be an integral part thereof. The IV bag 10 contains a medical fluid 12 therein, such as a therapeutic, diagnostic or nutritional preparation. The medical fluid 12 may be pre-sterilized in bulk prior to its transfer to the IV bag, or it may be sterilized in the IV bag using sterilizing equipment and techniques known in the art. The IV bag further comprises a fluid exit port or tube 14 the distal end 16 of which is in communication with medical fluid 12 and the proximal end 18 of which is to slideably receive distal end 32 of multiple use universal connector 30. Alternatively, multiple use universal connector 30 may be integral with fluid exit port or tube 14 of IV bag 10. In both cases, fluid exit port or tube 14 is sealed into IV bag 10 by bottom seam 20 of IV bag 10. On the proximal end 34 of multiple use universal connector 30, cap 60 is mounted having internal thread means thereon for enclosing said proximal end 34. Prior to use, cap 60 is removed from multiple use universal connector 30 for engagement with a luer connector.

FIG. 2A shows the multiple use universal connector without the cap; FIG. 2B shows the multiple use universal connector with the cap; and FIG. 2D shows the cap, all views being shown in perspective.

Reference is now being made to FIGS. 3A, 3B, 3C, 4A and 4B.

Figure 3A:
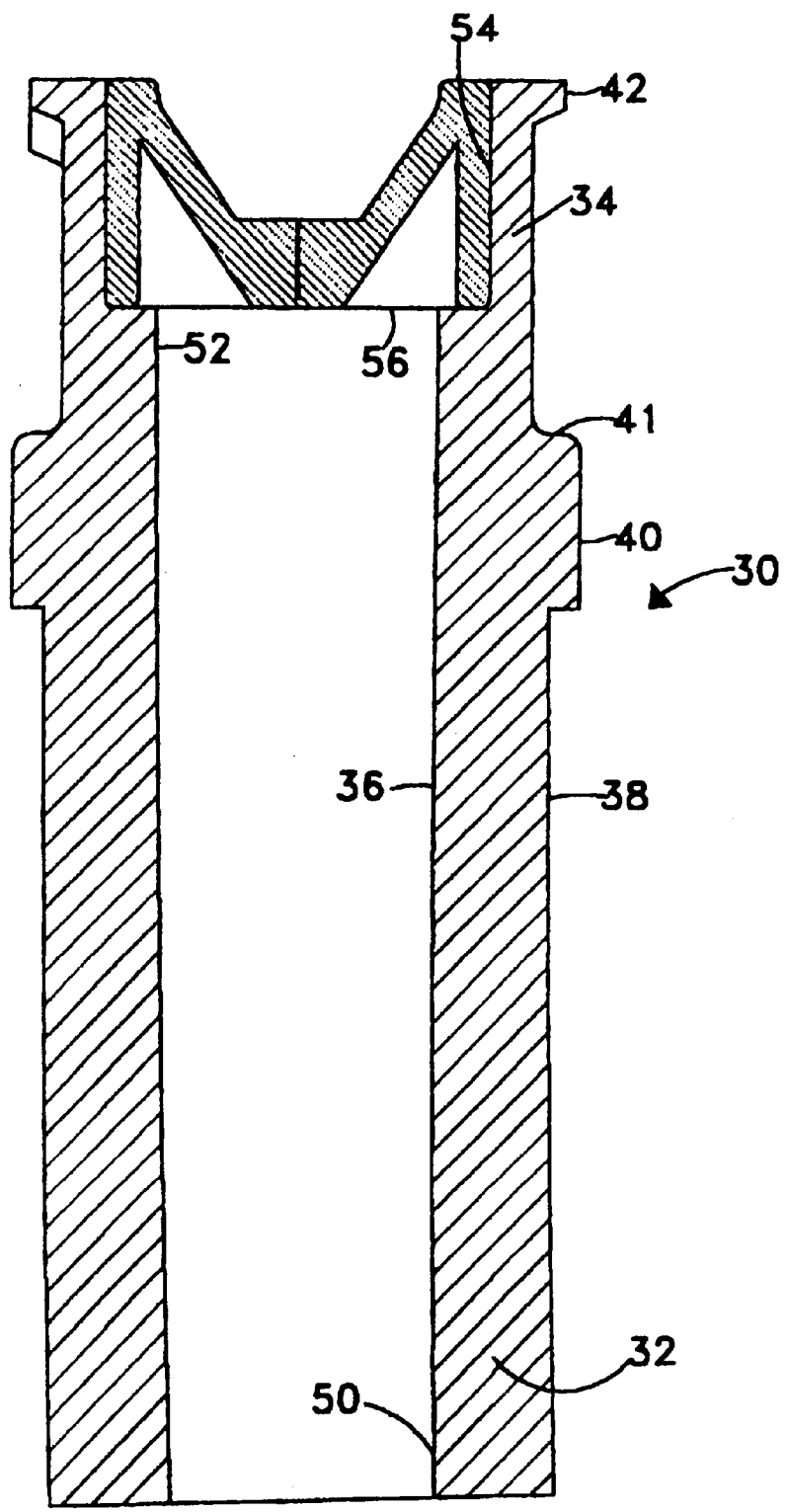
FIG. 3A is a cross-section of the multiple use universal connector without the cap attached taken along the line 3A—3A of FIG. 2A.

FIG. 3A shows a cross-sectional view of the multiple use universal connector without the cap taken along the line 3A—3A of FIG. 2A.

Figure 3B:
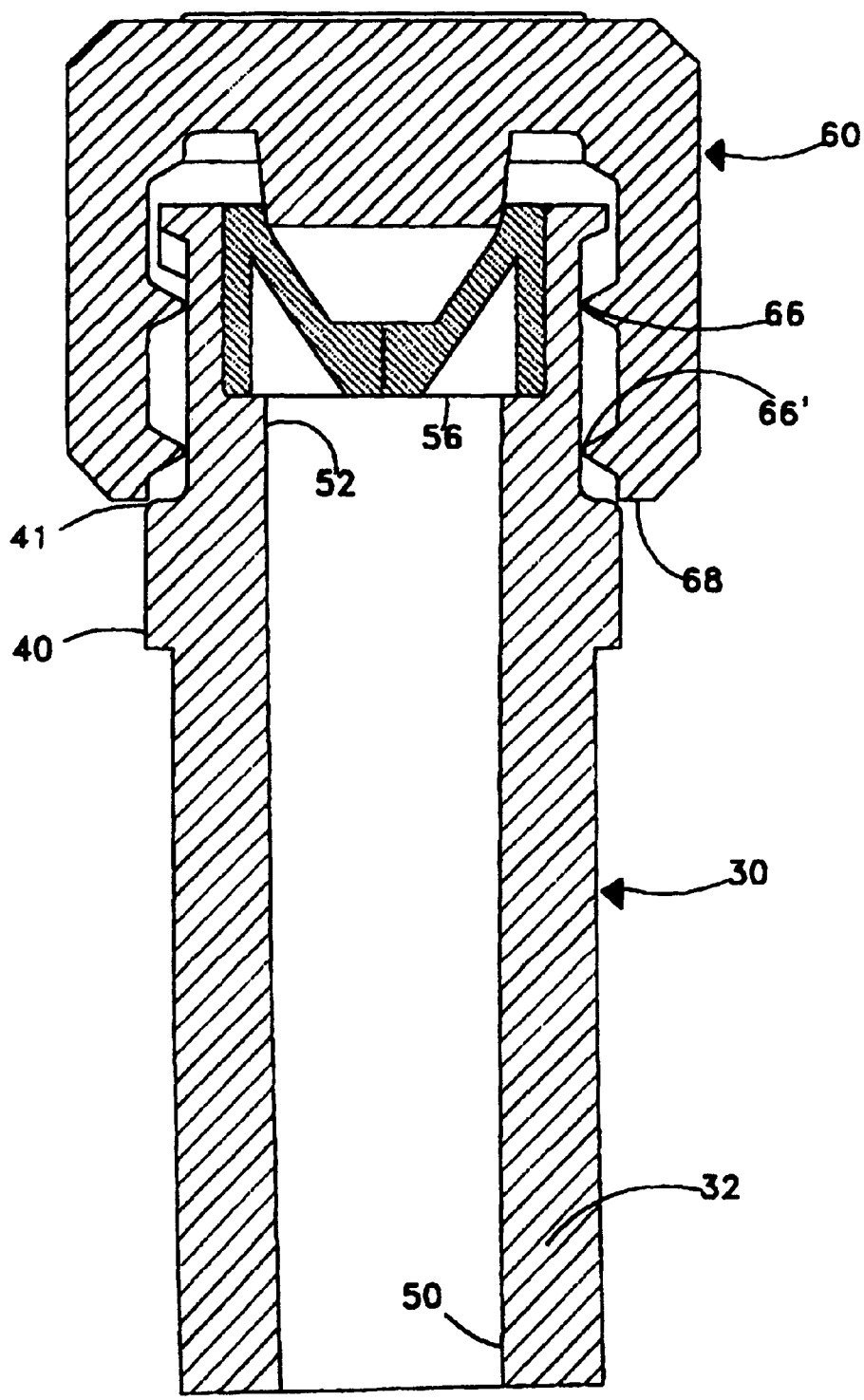
FIG. 3B is a cross-section of the multiple use universal connector with the cap attached taken along the line 3B—3B of FIG. 2B.

FIG. 3B shows the universal connector assembly taken along the line 3B—3B of FIG. 2B.

Figure 3C:
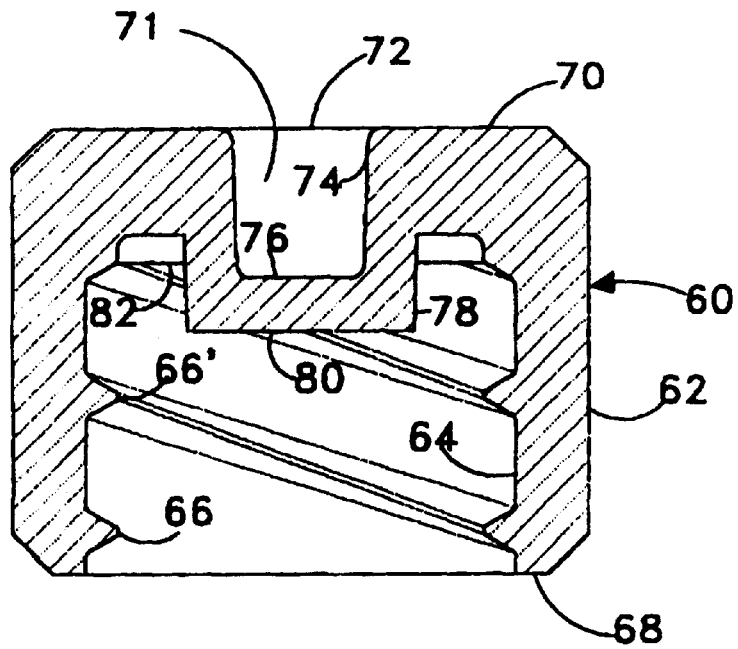
FIG. 3C is a cross-section of the cap taken along the line 3D—3D of FIG. 2D.
Figure 3D:
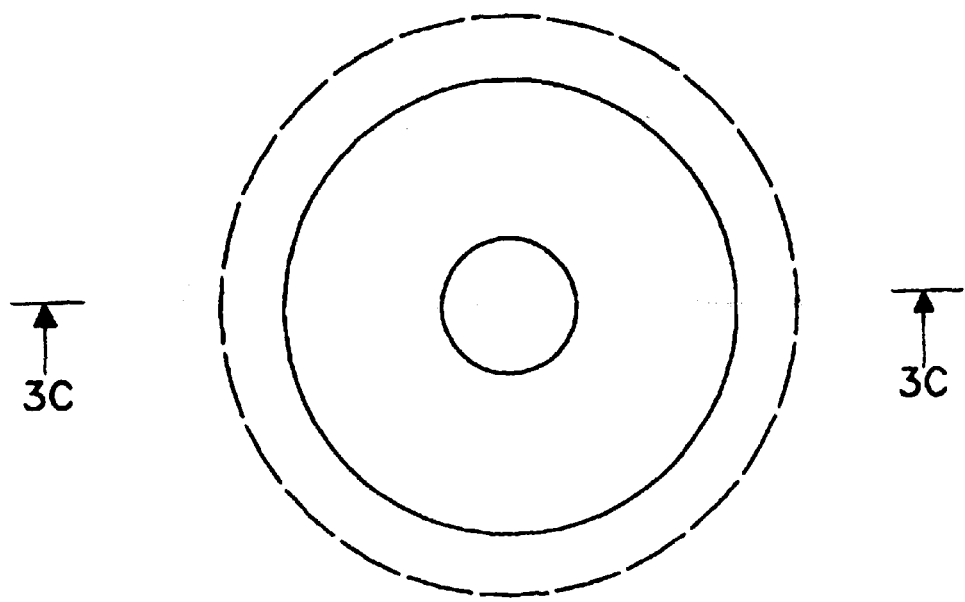
FIG. 3D is a top plan view of the cap shown in FIG. 2D.

FIG. 3C shows a cross-section of the cap taken along the line 3D—3D of FIG. 2D, and FIG. 3D shows the top plan view thereof.

The multiple use universal connector 30 is of tube-like configuration comprising: distal end 32 and proximal end 34; inside wall 36 and outside wall 38. Integral part of outside wall 38 at the proximal end 34 thereof is positioned first cap-locking ring 40 spaced from second cap-locking ring 42. First cap-locking ring serves as a male thread to receive cap 60 and to engage its internal threads 66 and 66'. Second cap-locking ring 42 having proximal end 41 has a larger external diameter than the distance defined by a line connecting internal threads 66–66' located at the proximal end 68 of cap 60. Second cap locking-ring 42 serves as stopping means for cap 60 when cap 60 is threaded onto the multiple use universal connector 30.

Inside wall 36 of multiple use universal connector 30 comprises: a distal end 50 and proximal end 52. Distal end 50 is designed to slideably and sealingly engage fluid exit port or tube 14 to slide into the fluid exit port through its proximal end 18.

At the proximal end 52 of multiple use universal connector 30 a cylindrical opening is defined by side wall 54 and bottom wall 56. The cylindrical opening is designed to receive cylindrical protuberance defined by outside walls 78 and 80 of cap 60.

Figure 4A:
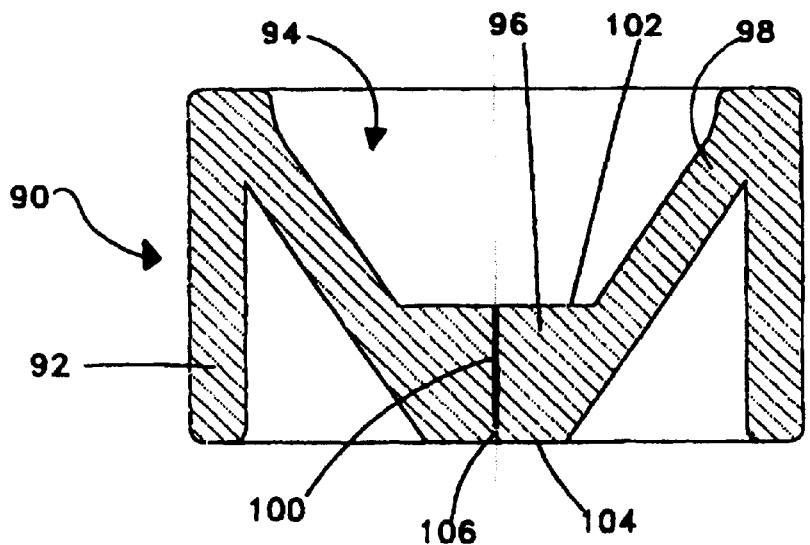
FIG. 4A is a greatly enlarged cross-section of the M-shaped diaphragm shown in FIG. 3A.

Bottom wall 56 and side wall 54 of cylindrical opening in multiple use universal connector 30, as best seen in FIG. 3B and FIG. 4A, contain an elastomeric diaphragm 90 bonded to the universal connector. The elastomeric diaphragm is of an M-shaped configuration and seals the fluid channel defined by the proximal end of inside wall 52 of universal connector 30. The diaphragm is of inert gas-impermeable polymeric material capable of flexing under internal or external pressures such as exerted during steam sterilization. The diaphragm has a durometer of from about 25 to about 80 Shore A. Suitable elastomeric materials for constructing the diaphragm include:

natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene fluoride-tetrafluoroethylene terpolymers, such as sold under the tradenames of Fluorel and Viton;

butyl rubbers;

polyisobutene, such as sold under the tradename Vistanex;

synthetic polyisoprene rubber;

silicone rubbers;

styrene-butadiene rubbers;
tetrafluoroethylene propylene copolymers; and
thermoplastic-copolyesters.

Figure 4B:
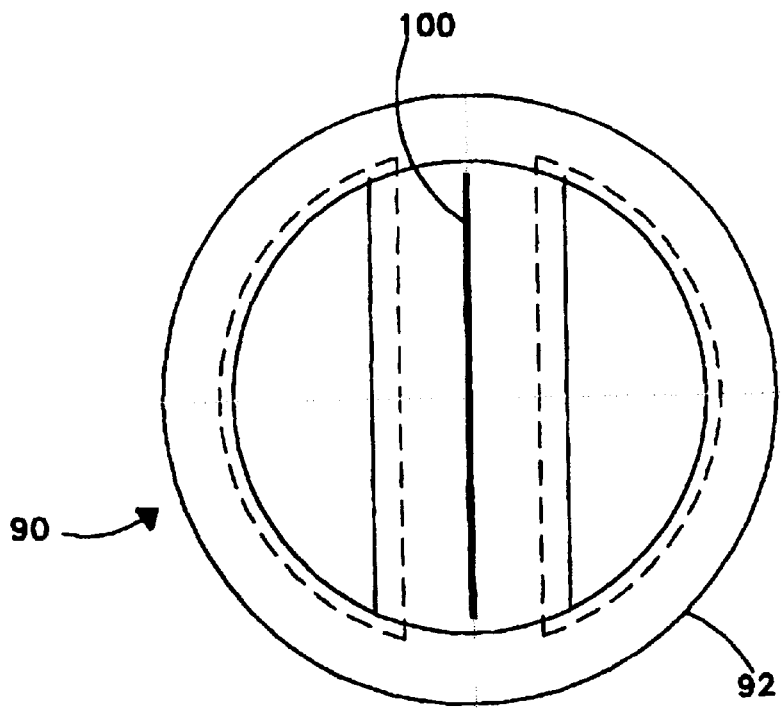
FIG. 4B is a top plan view of the M-shaped diaphragm shown in FIG. 4A.

As best seen in FIGS. 4A and 4B, M-shaped diaphragm 90 comprises leg portion 92 and cup-shaped portion 94. Cup-shaped portion comprises:

a horizontal bottom portion 96; and side portion 98 which enclose an obtuse angle between them. Leg portion 92 and side portion 98 typically have a thickness of from about 0.1 to 6 mm, while bottom portion 96 typically has a thickness of from about 1 to 20 mm.

The horizontal bottom portion 96 is provided with a slit 100 which extends from the top surface 102 of the horizontal bottom portion toward the bottom surface 104. However, the slit does not penetrate the bottom surface. The unpenetrated membrane, denoted by the numeral 106, is typically of from about 0.001 mm to about 2.0 mm. The unpenetrated membrane maintains the content of the container, in which the multiple use universal connector is used, in sealed condition. In use, when this membrane is ruptured by an external access means, such as a needle cannula, luer connector or spike, fluid communication is established between the content of the container and the external access means. Upon disengaging the external access means for the multiple use universal connector, the cup-shaped portion of the diaphragm reseals itself for the reason that the membrane is resilient and springs back to its original configuration. As a result the container is resealed until the fluid withdrawal process is repeated.

As best seen in FIGS. 3C and 3D, cap 60 is designed for securely closing multiple use universal connector 30 at the proximal end 34 thereof, and protecting elastomeric diaphragm 90 from contact with the outside environment. The configuration of the cap closely approximates the luer connector shown in FIG. 6 which, in addition to the features detailed as the description of the cap proceeds, also contain a tubing conduit which is part of the luer connector. FIGS. 3C and 3D show cylindrical cap 60 comprising: outside wall 62 and inside wall 64. Outside wall 62 comprises: bottom wall 68; top wall 70; and central portion 72 of top wall 70. Inside wall 64 comprises: internal threads 66 and 66' extending towards the center of the cap; a cylindrical protuberance defined by outside wall 78 and bottom wall 80 extending distally into the space defined by the inside wall; and shoulder portion 82 connecting inside wall 64 and outside wall 78 of the cylindrical protuberance. In the proximal end of cap 60 there is located plug 71 defined by central portion 72 of top wall 70, and bottom wall 76. Plug 71 may be integral with the cap such as obtained by blow molding technique or the plug may be manufactured separately and subsequently sealed into the cap.

Referring again to FIGS. 3B and 3C, when cap 60 is threaded onto universal multiple use connector 30, bottom wall of protuberance 80 will be spaced from elastomeric diaphragm 90 allowing the membrane to flex outward under pressure, such as created during heat sterilization. However, spacing should not be more than about 0.1 to 3 mm so that under accidentally high pressures bursting of the membrane is prevented by the support of bottom wall 80 of cylindrical protuberance.

Figure 5A:
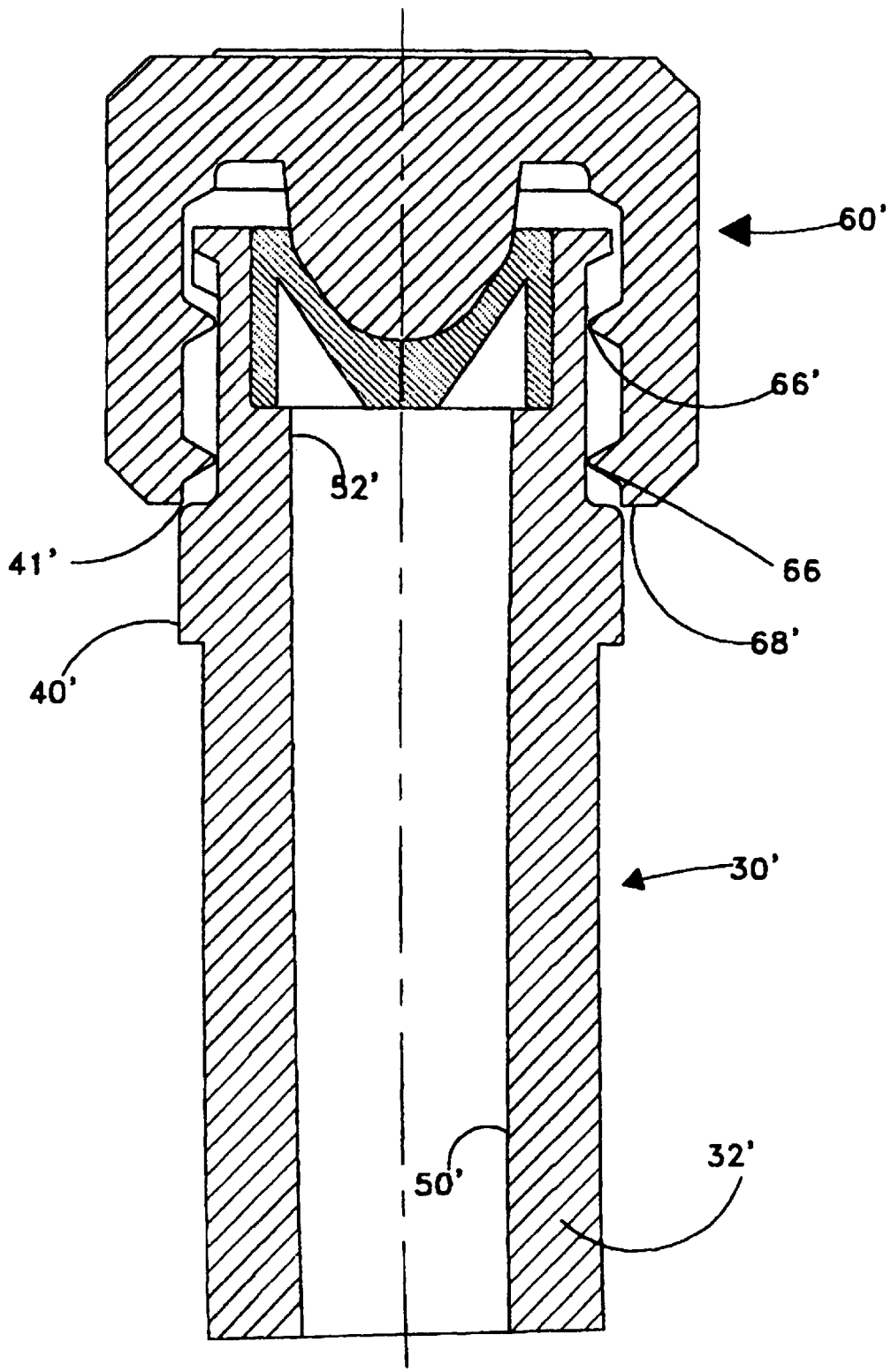
FIG. 5A is a cross-sectional view of another embodiment of the multiple use universal connector with the cap attached, wherein the M-shaped diaphragm has a smooth, semi-circular top surface.
Figure 5B:
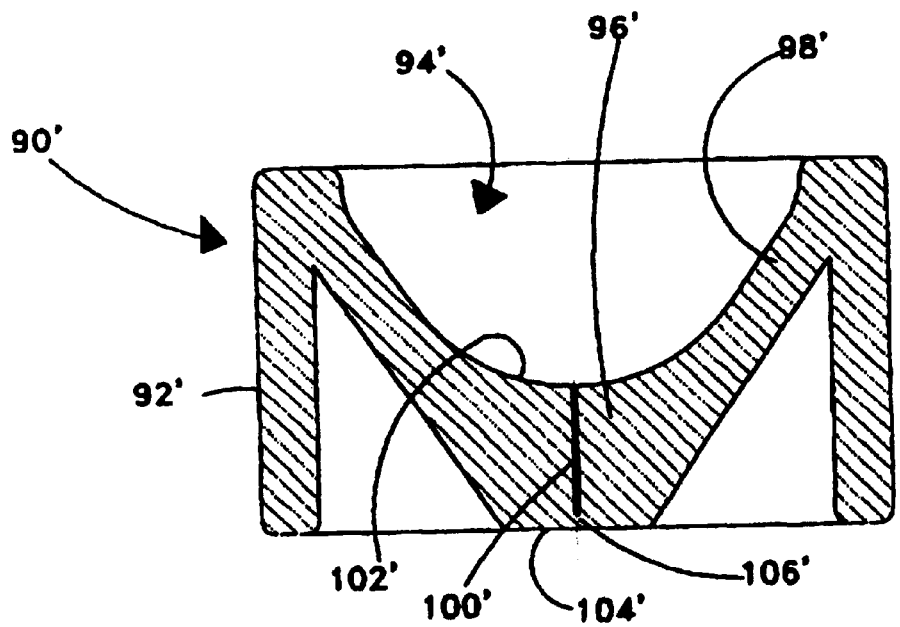
FIG. 5B is a greatly enlarged cross-section of the M-shaped diaphragm shown in FIG. 5A.
Figure 5C:
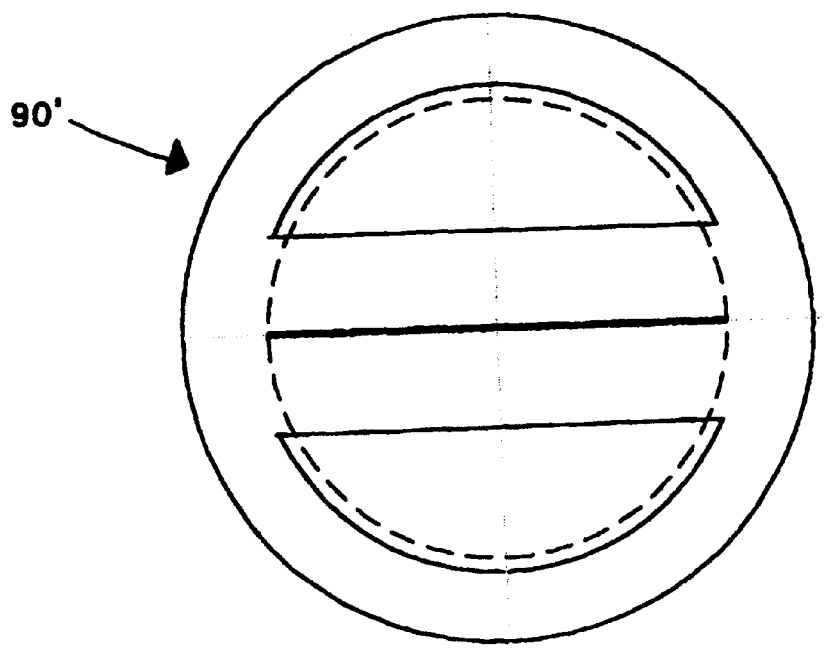
FIG. 5C is a top plan view of the M-shaped diaphragm shown in FIG. 5B.

FIGS. 5A, 5B and 5C show another embodiment of the multiple use universal connector of the present invention. FIG. 5A shows a cross-sectional view with the cap attached. FIG. 5B shows a cross-sectional view of an M-shaped diaphragm and FIG. 5C shows a top plan view thereof. In these figures the numbers with prime (') denote the same parts as in FIGS. 3A, 3B, 3C, 3D, 4A and 4B. In this embodiment the M-shaped diaphragm 90' comprises: leg portion 92'; and cup-shaped portion 94'. Cup-shaped portion comprises: horizontal bottom portion 96'; and side portion 98' which enclose a semi-circular surface 102'. Leg portion 92' and side portion 98' typically have a thickness of from about 0.1 to 6 mm, while bottom proton 96' typically have a thickness of from about 1 to 20 mm.

The horizontal bottom portion 96' is provided with slit 100' which extends from the top semi-circular surface 102' of the horizontal bottom portion toward the bottom surface 104. However, the slit does not penetrate the bottom surface. The unpenetrated membrane, denoted by the numeral 106' is typically of from about 0.001 mm to about 2.0 mm. The unpenetrated membrane maintains the content of the container, in which the multiple use universal connector is used, in sealed condition.

In use, when this membrane is ruptured by an external access means, such as a needle cannula, luer connector or spike, fluid communication is established between the content of the container and the external access means. Upon disengaging the external access means for the multiple use universal connector, the cup-shaped portion of the diaphragm reseals itself for the reason that the membrane is resilient and springs back to its original configuration. As a result the container is resealed until the fluid withdrawal process is repeated.

We have found that both configurations of the M-shaped diaphragm perform well in resealing themselves in multiple use.

Figure 6:
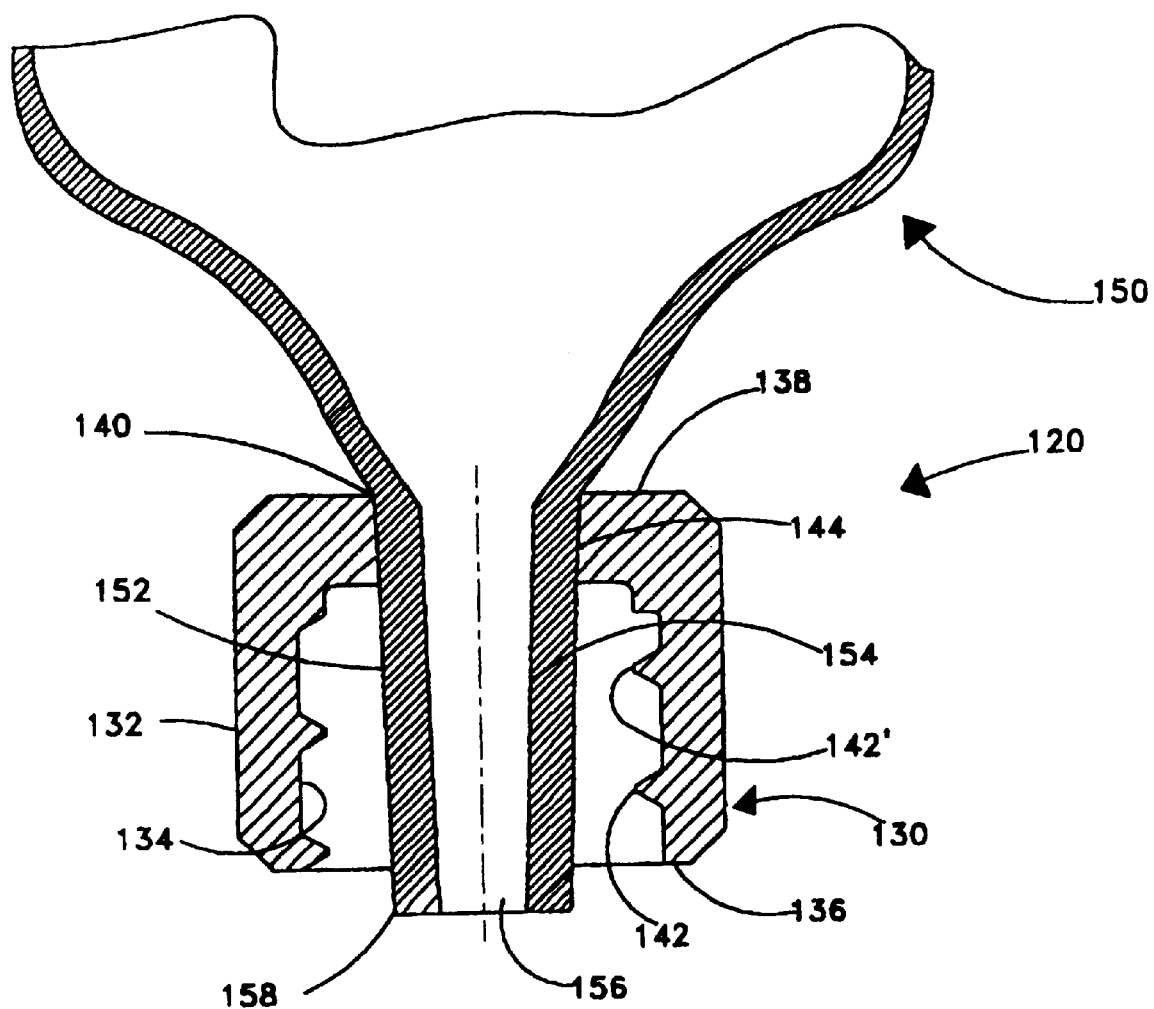
FIG. 6 is a cross-section of a luer connector attachable to the multiple use universal connector of the present invention.

FIG. 6 shows in cross-sectional view a luer connector attachable to each of the embodiments of the present invention. The luer connector 120 comprises a cylindrical cap 130 and tubing conduit 150. Cylindrical cap 130 closely approximates cylindrical cap 60 of the multiple use universal connector shown in FIGS. 3B and 3C and its function is to be threaded onto the multiple use universal connector when fluid communication is desired. Prior to threading cylindrical cap 130 of luer connector 120 onto the multiple use universal connector 30, cylindrical cap 60 is removed and then replaced by cylindrical cap 130 of luer-connector 120.

Cylindrical cap 130 of luer connector 120 comprises outside wall 132 and inside wall 134. Outside wall 132 comprises: bottom wall portion 136; top wall portion 138; and central portion 140 of top wall portion 138. Inside wall 134 comprises: internal threads 142 and 142' extending towards the center of the cap.

Tubing conduit 150 is positioned in cylindrical cap 130 of luer connector 120 at its top central portion 140. Thickened outside wall portion 144 parallelly faces outside wall 152 of tubing conduit 150 and is permanently attached thereto by adhesive or other suitable means known in the art. Tubing conduit further comprises: inside wall of tubing conduit 154 forming a fluid channel 156; and bottom end portion of tubing conduit 158 which extends beyond bottom portion 136 of cylindrical cap 130 of cylindrical cap of luer connector. When threaded onto multiple use universal connector 30, luer connector 120 travels towards second cap-locking ring 142, contacts diaphragm membrane 90 or 90' with its bottom and portion 158 and exerts pressure thereon in a twisting motion. The exerted force ruptures the elastomeric membrane thereby allowing fluid communication between the luer connector 120 and the content of the intravenous infusion bag.

The multiple use universal connector 30 and 30' may also be used in containers, such as bottles and vials the contents of which are intended to be accessed by a hypodermic syringe having either a sharp or blunt cannula. When fluid withdrawal or fluid addition is desired, cylindrical cap 60 or 60' of multiple use universal connector 30 or 30' is removed and the diaphragm is pierced by the cannula providing access to the content of the container or its withdrawal therefrom.

Figure 7A:
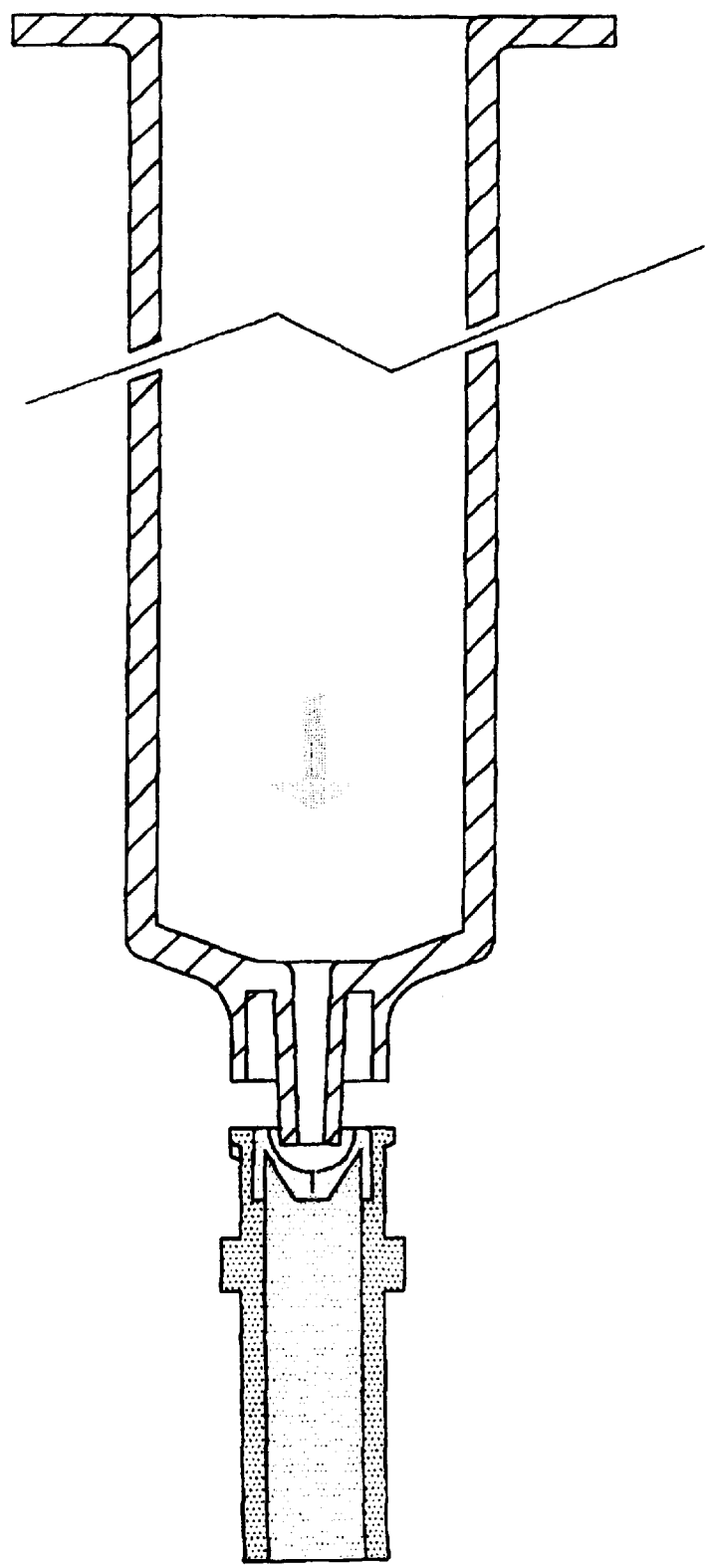
FIG. 7A is a cross-section of the multiple use universal connector prior to penetration of the diaphragm by the luer connector of a syringe.
Figure 7B:
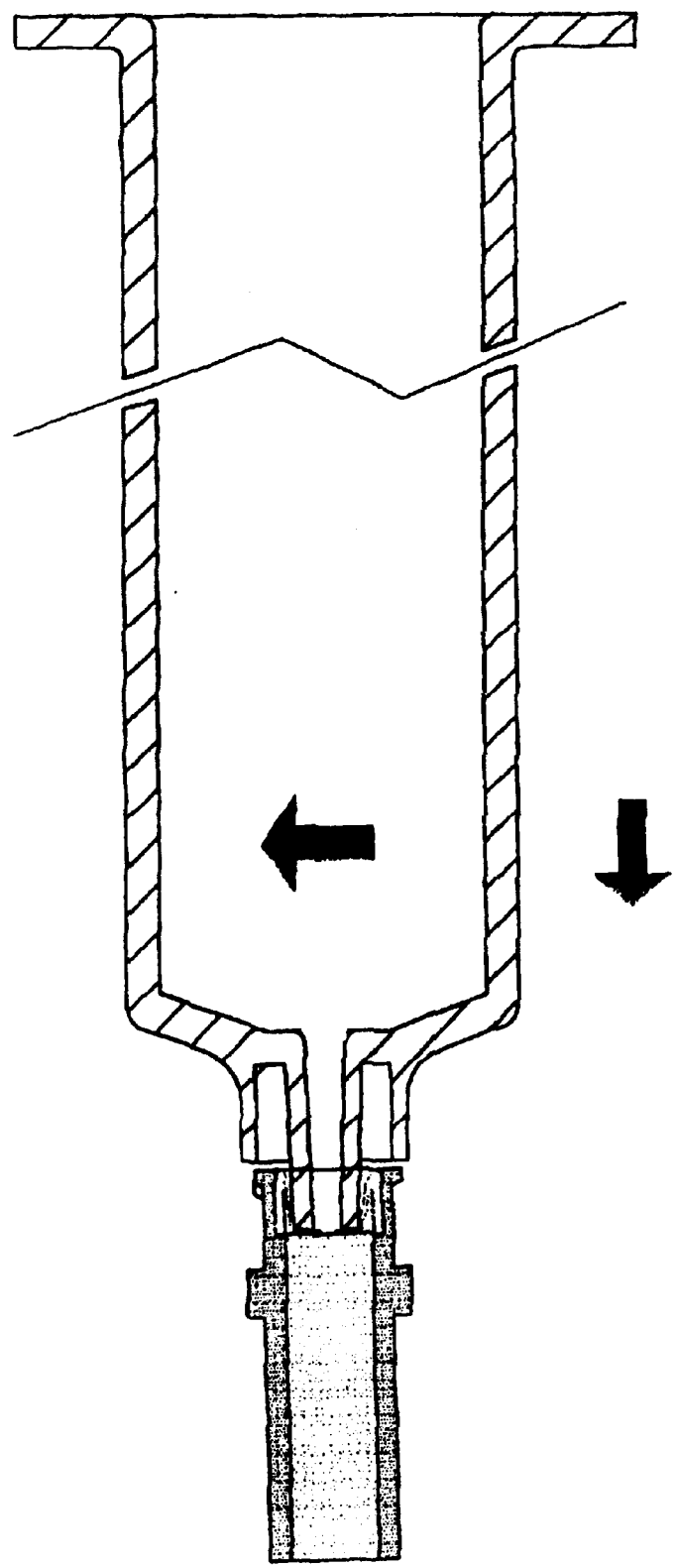
FIG. 7B is a cross-section of the multiple use universal connector at initial penetration and break-through of the diaphragm by the luer connector of a syringe.
Figure 7C:
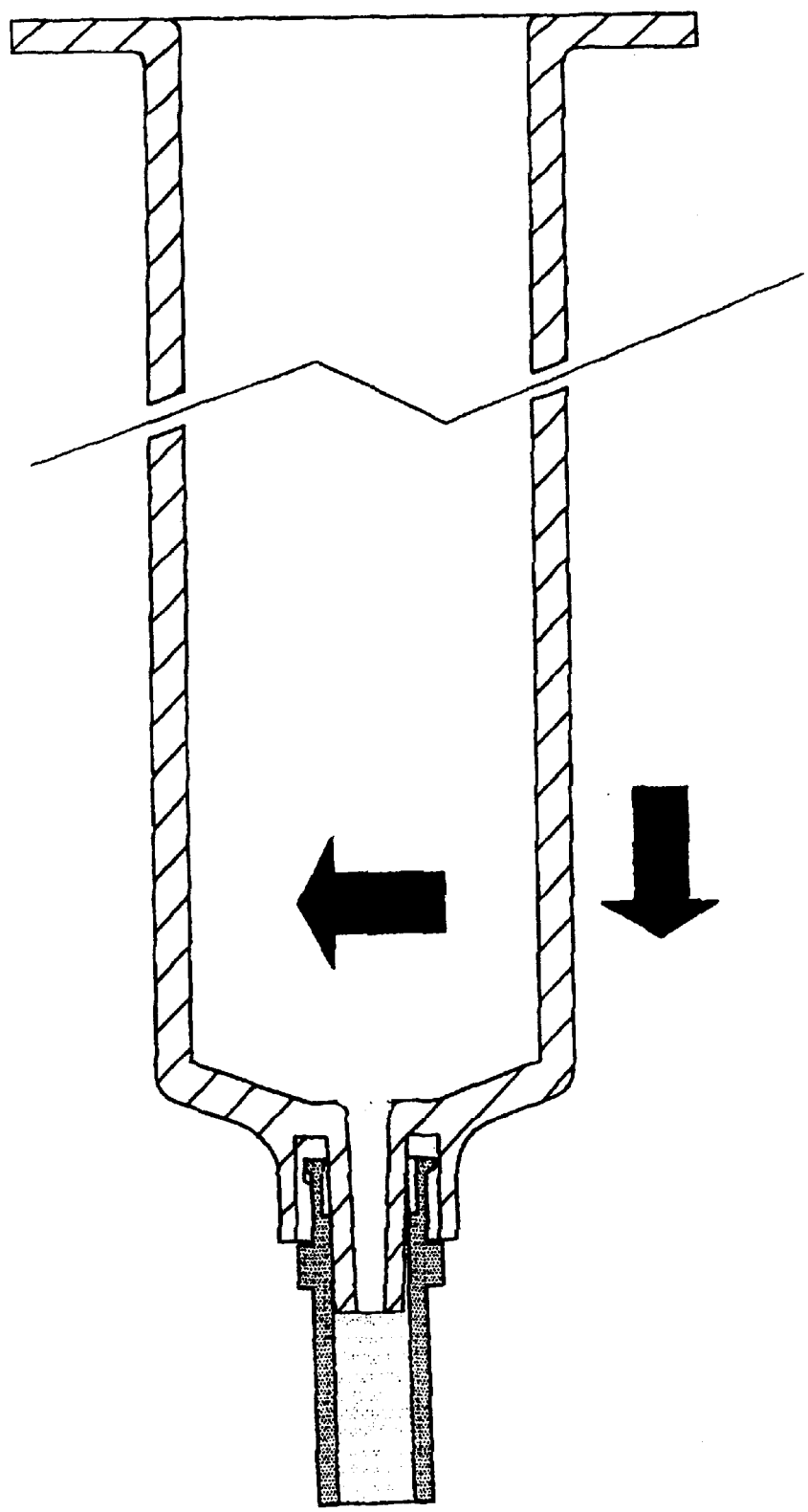
FIG. 7C is a cross-section of the multiple use universal connector at complete penetration of the diaphragm by a luer connector whereby full flow access of the content of the container is achieved.
Figure 7D:
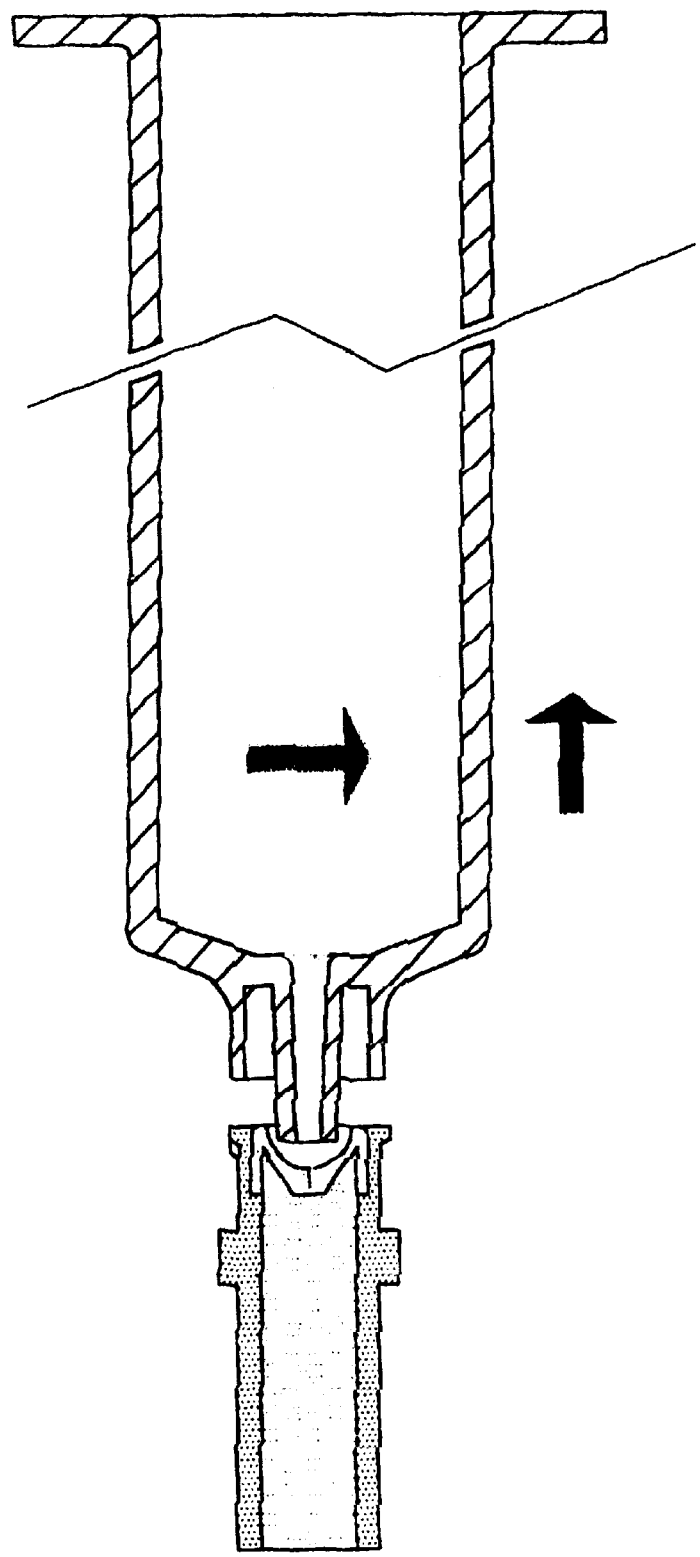
FIG. 7D is a cross-section of the multiple use universal connector after removal of a luer connector whereby the diaphragm reseals itself.

FIG. 7A is a cross-section of the multiple use universal connector prior to penetration of the diaphragm by the luer connector of a syringe;

FIG. 7B is a cross-section of the multiple use universal connector at initial penetration and break-through of the diaphragm by the luer connector of a syringe;

FIG. 7C is a cross-section of the multiple use universal connector at complete penetration of the diaphragm by a luer connector whereby full flow access of the content of the container (not shown) is achieved; and FIG. 7D is a cross-section of the multiple use universal connector after removal of a luer connector whereby the diaphragm reseals itself.

Figure 8:
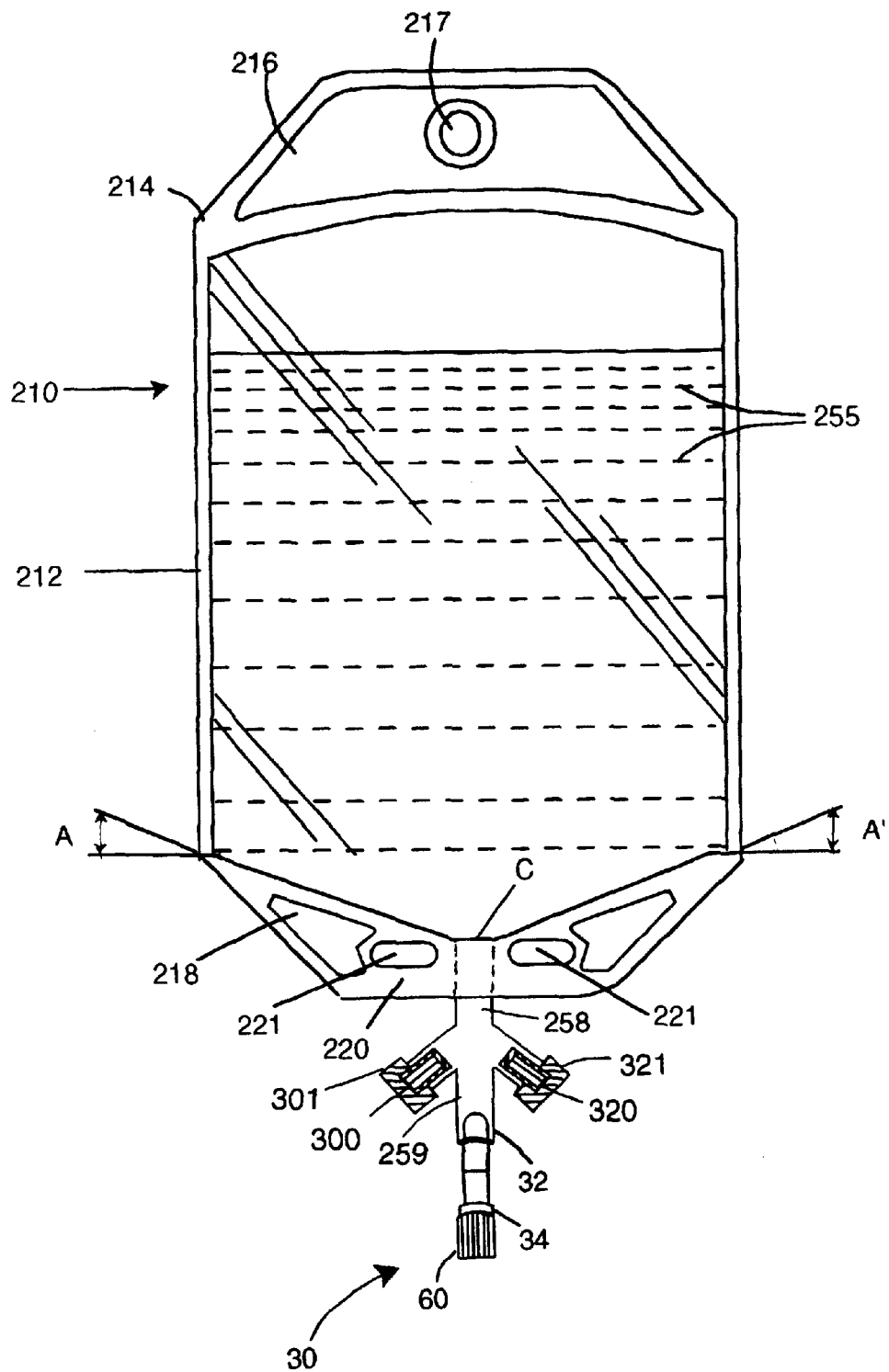
FIG. 8 is a plan view of a universal flexible container multiple use universal connector assembly in accordance with the present invention showing:
a) a pouch; and
b) a combination access member of inverted Y shape configuration having a stem with proximal and distal ends and a pair of tines comprising:
1) an IV access port to which the multiple use universal connector is sealably attached;
2) a needle access port located in one of the tines of the combination access member; and
3) a spike access port located in the other of the tines of the combination access member.
Figure 9:
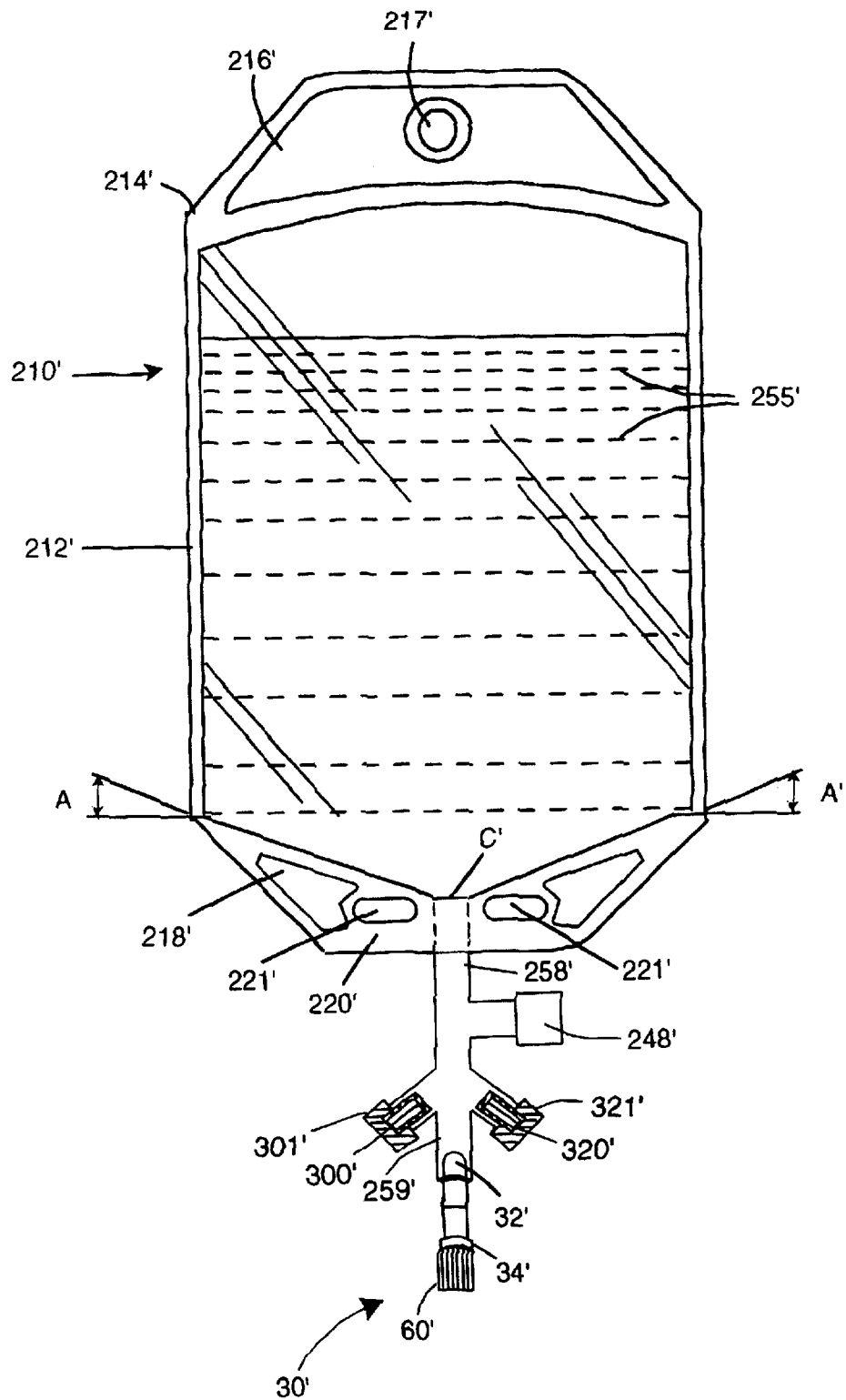
FIG. 9 is a plan view of another embodiment of the present invention showing:
a) a pouch; and
b) a combination access member of inverted Y shape configuration having a stem with proximal and distal ends and a pair of tines comprising:
1) an IV access port to which the multiple use universal connector is sealably attached, said IV access port is equipped with a vent;
2) a needle access port located in one of the tines of the combination access member; and
3) a spike access member located in the other of the tines of the combination access member.

In the first preferred embodiment the present invention provides a universal, flexible plastic container, in the shape of a bag, pouch or bottle, for the containment and delivery of diagnostic contrast media, nutrients and drug formulations. In the drawings where like numerals indicate like elements or portions, the reference character 210 and 210' in FIGS. 8 and 9 indicate the container which, in a preferred embodiment, is a pouch-like device, comprising two superimposed sheets of suitable length and width made of flexible or pliable materials, such as polymeric materials including polyethylene, polypropylene, and preferably thermoplastic materials. The superimposed sheets forming the pouch-like container are preferably made of transparent materials so as to allow observation of the amount of its content during the filling operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably flat welded to each other so as to form the pouch whose volume is zero before it is filled with a parenteral solution. When the pouch is filled or partially filled as shown by 255 in FIG. 8 and 255' in FIG. 19, it assumes the shape of a small cushion. The superimposed sheets are joined together along marginal areas 212, 212', 214, 214', 216, 216', 218, 218', 220 and 220' as shown in FIGS. 8 and 9 respectively.

The bottom portion of pouch 210 or 210' terminates in first angle A and second angle A' from the center C or C' of said bottom portion and relative to a horizontal plane crossing the center C or C' of said bottom portion to direct and facilitate the flow of content contained in the pouch towards a combination access member of inverted Y shape configuration 258 or 258'. Angles A and A' are of from about 5° to about 45°, preferably from 10° to 30° and most preferably from 10 to 20°.

Combination access member, having an inverted Y shape configuration is located at center C or C' of the bottom portion of pouch 210 or 210' comprising:

a steam having a proximal end 258 or 258' and a distal end 259 or 259'; and a pair of tines integral with the stem. The proximal end 258 or 258' is located at the bottom center portion of the pouch and below a horizontal plane crossing the center C or C' of said bottom portion so that all the liquid content of the pouch can be drained from the pouch into the stem. The proximal end 258 or 258' is sealed between the two superimposed sheets in the periphery thereof which form the pouch.

A pair of tines extend from and are integral with the stem forming the inverted Y shape of the combination access member. One of the tines constitutes the needle access port 300 or 300' and is covered by cap 301 or 301'. The other of the tines constitutes the spike access port 320 or 320' and is covered by cap 321 or 321'. The cap covering the needle and spike access ports maintain sterility of content of the pouch until the point of use.

Referring to FIGS. 8 and 9, the stem of the combination access member is sealably attached at its distal end 259 or 259' to the multiple use universal connector 30 or 30'.

Referring to FIGS. 8 and 9, access to needle access port 300 or 300' using a steel needle is gained by removing caps 301 or 301'. Access to spike access port 320 or 320' using a plastic spike is gained by removing caps 301 or 301'.

Marginal areas 316 and 316' in FIGS. 8 and 9 preferably comprise at least one hole 217 or 217' for suspending the pouch when it is in use for delivering the content of the pouch to a delivery site.

Marginal areas 220 and 220' in FIGS. 8 and 9 preferably comprise at least one, and more preferably a plurality, of hole(s) 221 and 221' to facilitate suspending the pouch during the filling process.

The universal, flexible container of the present invention may be used for delivering a single dose or multi-dose of parenteral solution. The needle and spike access ports, along with the IV access port equipped with the multiple use universal connector, allow access to the drug in the pouch by means that happen to be available under any circumstances.

In addition to providing multiple access ports, the present invention provides further improvement in flexible containers designed for delivering parenteral solutions, such as diagnostic contrast media and drug formulations.

It was discovered that if the inside wall of the first sheet or the second sheet forming the pouch 210 of FIG. 8 or pouch 210' of FIG. 9 is embossed, fluid hold up in the form of drops adhering to the inside walls can be reduced or eliminated and the walls, as the content of the pouch is being drained into the injection site, adhering together and further trapping drops of the fluid, can be prevented. In accordance with this discovery there are provided the following preferred embodiments of the invention.

Figure 10A:
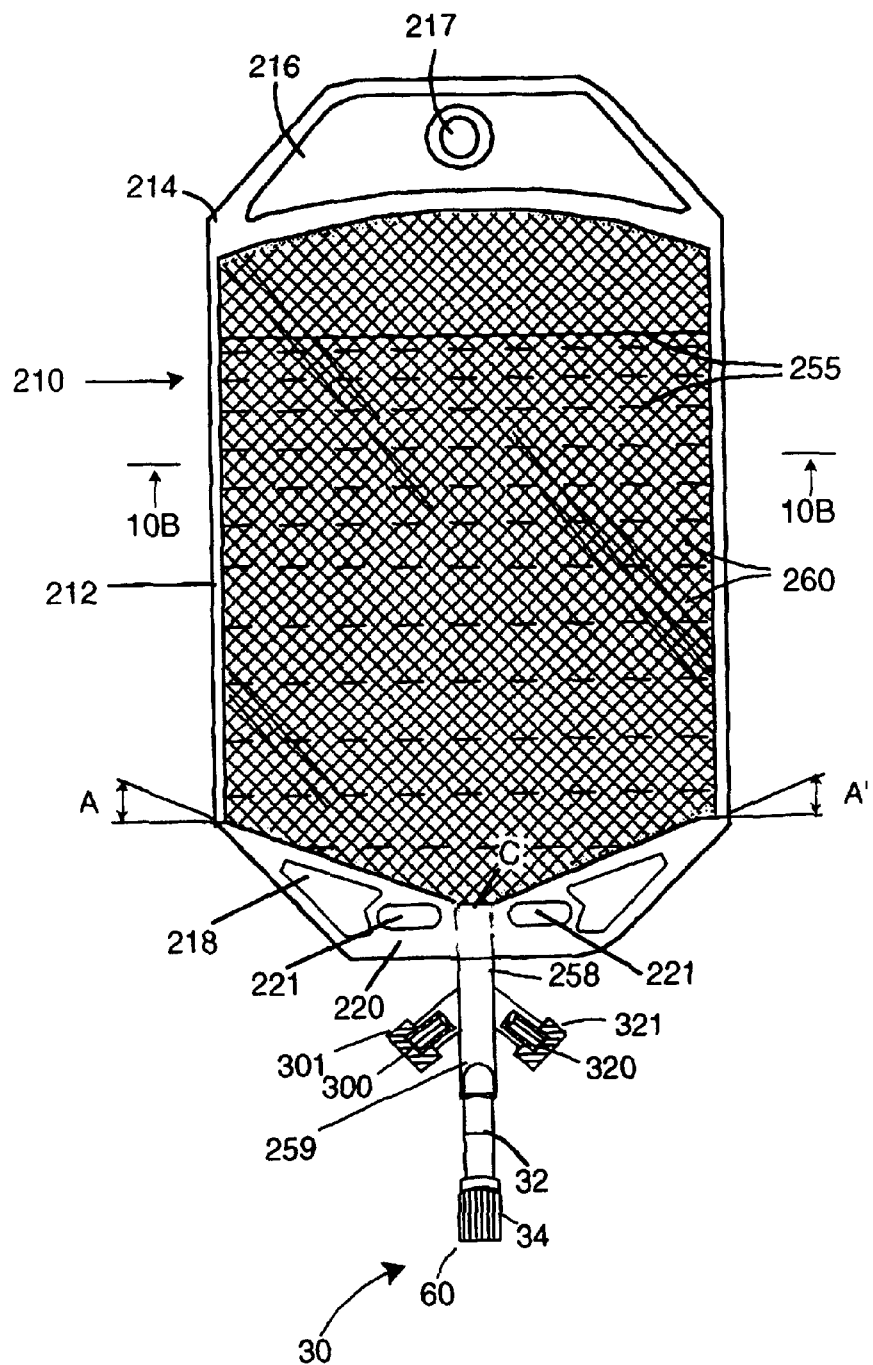
FIG. 10A is plan view of the universal, flexible container multiple use universal connector assembly shown in FIG. 8 one wall of which is embossed in a checkerboard fashion.
Figure 10B:
FIG. 10B is a cross-section of the universal, flexible container multiple use universal connector assembly shown in FIG. 10A taken along the line 10B—10B.

Referring to FIG. 10A and FIG. 10B, the inside wall of first sheet of pouch 210 shown in FIG. 8 is embossed in a checkerboard manner 260, the checkerboard consisting of squares the 90° angles of which pointing downward towards the center C of the pouch. The size of the individual squares may be in the range of from 0.01 to 10 mm$^2$ or larger. The size of the individual squares may vary the determination of which would be influenced by the viscosity and the surface tension of the parenteral liquid for the delivery of which the pouch is intended.

While the inside wall of both first sheet and second sheet may be embossed, it was observed that the pouch functions better in terms of eliminating fluid hold up and preventing the superimposed walls from sticking together when only one inside wall of the first or second sheet is embossed.

FIG. 11A and FIG. 11B show the embodiment described in FIG. 9, except that the inside wall of first sheet of pouch 210' is embossed as described in FIGS. 10A and 10B.

Figure 12A:
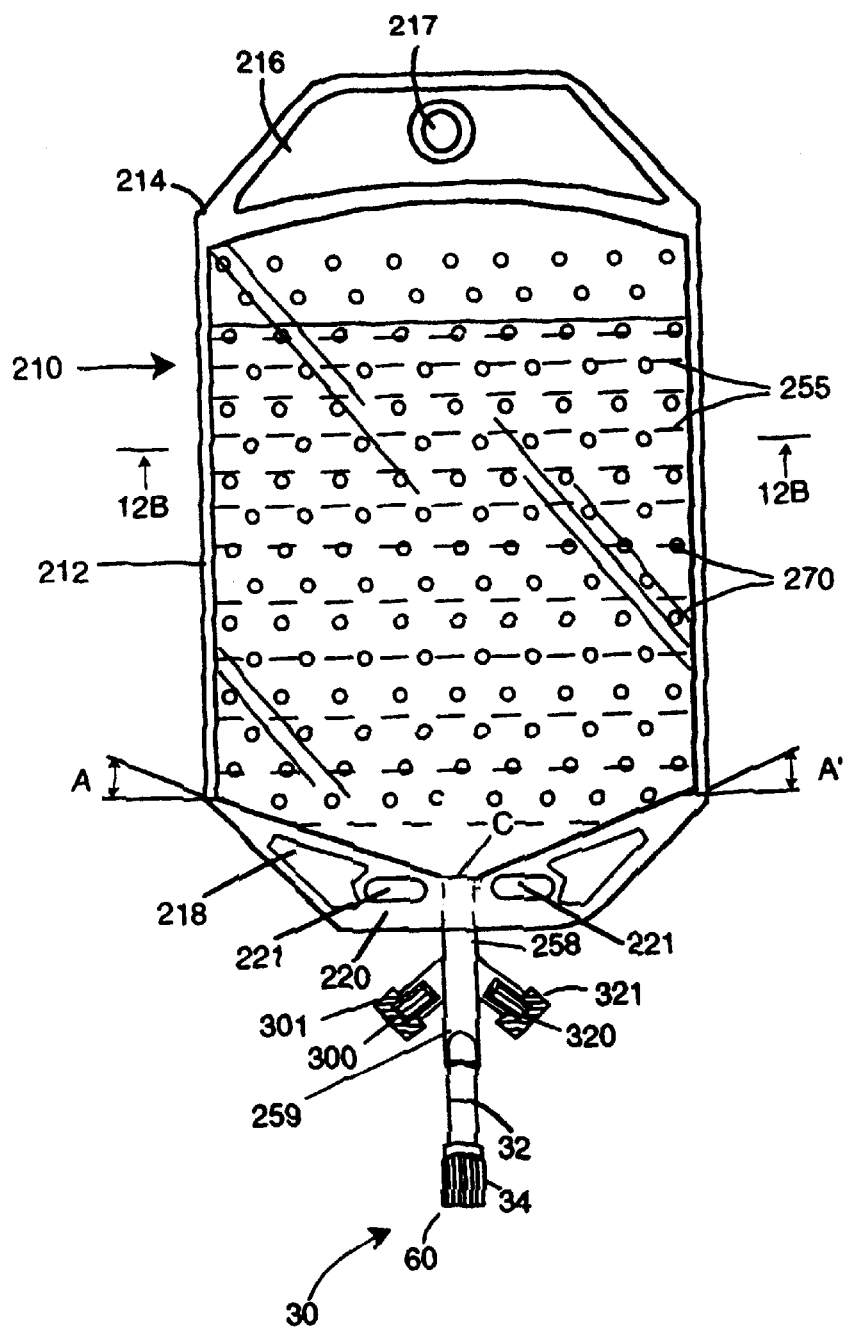
FIG. 12A is a plan view of the universal, flexible container multiple use universal connector assembly shown in FIG. 8 one wall of which is embossed in a dotted fashion.
Figure 12B:
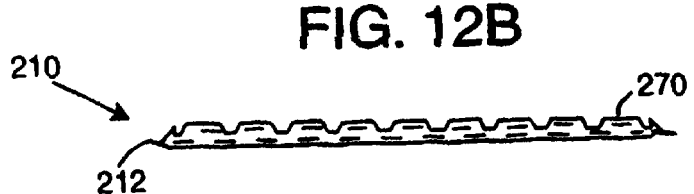
FIG. 12B is a cross-section of the universal, flexible container multiple use universal connector assembly shown in FIG. 12A taken along the line 12B—12B.

Referring to FIG. 12A and FIG. 12B, the inside wall of first sheet of pouch 210 of FIG. 8 is embossed with dots or micro circles 70 in a spaced relationship from each other. The dots or circles may vary in diameter from 5 microns to several mms and may be spaced from each other of from about 10 microns to about 10 mms or longer. While both inside walls of the first sheet and second sheet may be embossed, it is preferred that only the first sheet or second sheet be embossed.

Figure 13A:
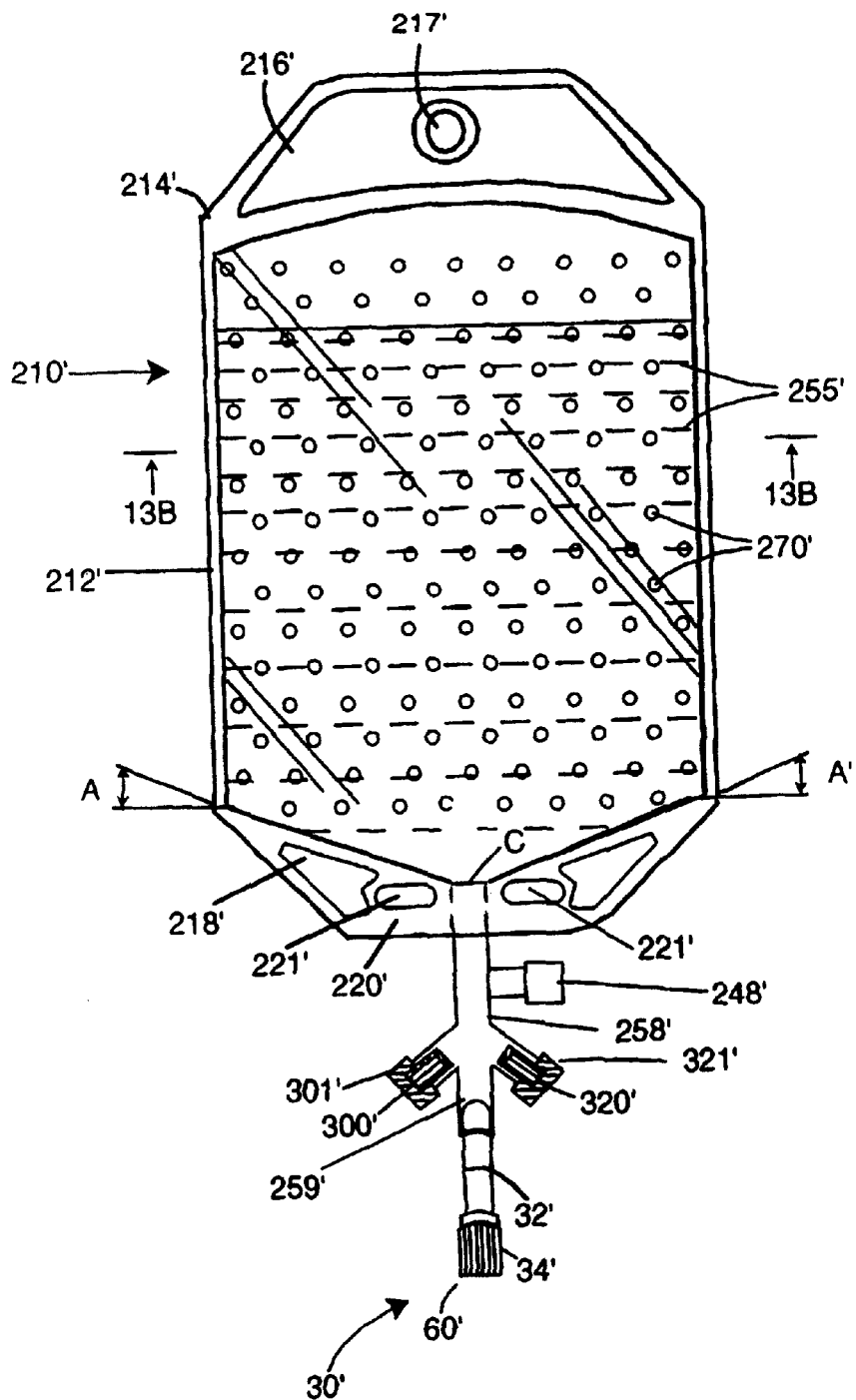
FIG. 13A is a plan view of the universal, flexible container multiple use universal connector assembly shown in FIG. 9 one wall of which is embossed in a dotted fashion.
Figure 13B:
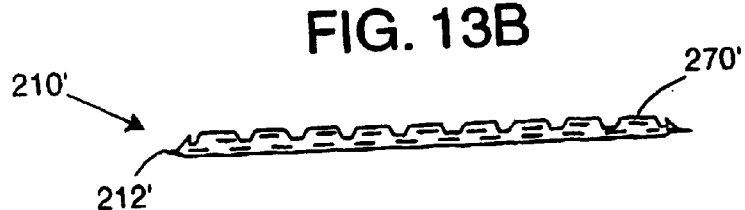
FIG. 13B is a cross-section of the universal, flexible container multiple use universal connector assembly shown in FIG. 13A taken along the line 13B—13B.

FIG. 13A and FIG. 13B show the embodiment described in FIG. 9, except that the inside wall of first sheet of pouch 210' is embossed 270' as described in FIGS. 12A and 12B.

Figure 14A:
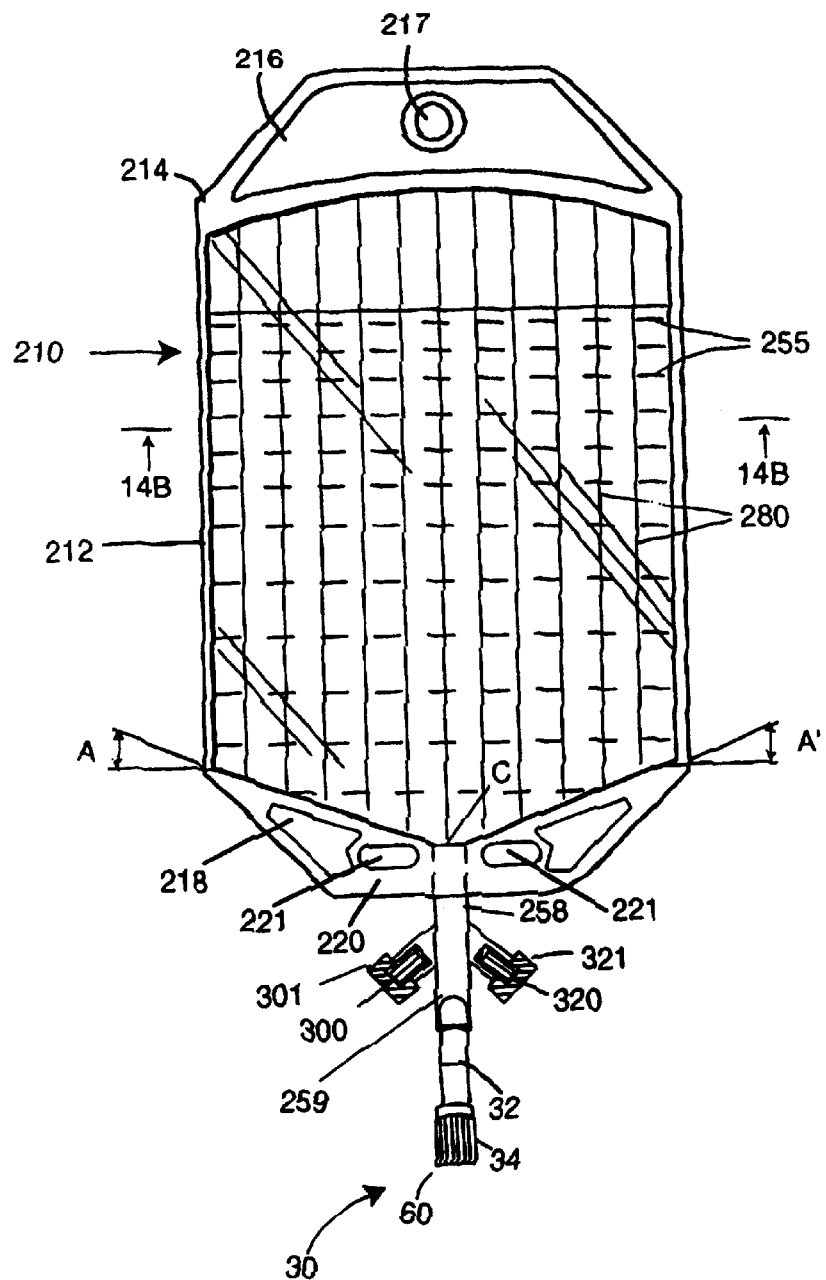
FIG. 14A is a plan view of the universal, flexible container multiple use universal connector assembly shown in FIG. 8 one wall of which is embossed with vertically oriented channels.
Figure 14B:
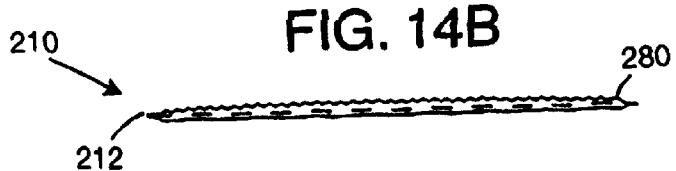
FIG. 14B is a cross-section of the universal, flexible container multiple use universal connector assembly shown in FIG. 14A taken along the line 14B—14B.

Referring to FIGS. 14A and 14B, the inside wall of first sheet of pouch 210 shown in FIG. 8 is embossed 280 in vertical channel configuration in spaced relationship from each other. The width of the individual channels may be in the range of from about 0.01 to about 10 mm or larger. The channels may be spaced from each other of from about 10 microns to about 10 mms. While both inside walls of the first sheet and second sheet may be embossed, it is preferred that only one inside wall of the first or second sheet be embossed.

Figure 15A:
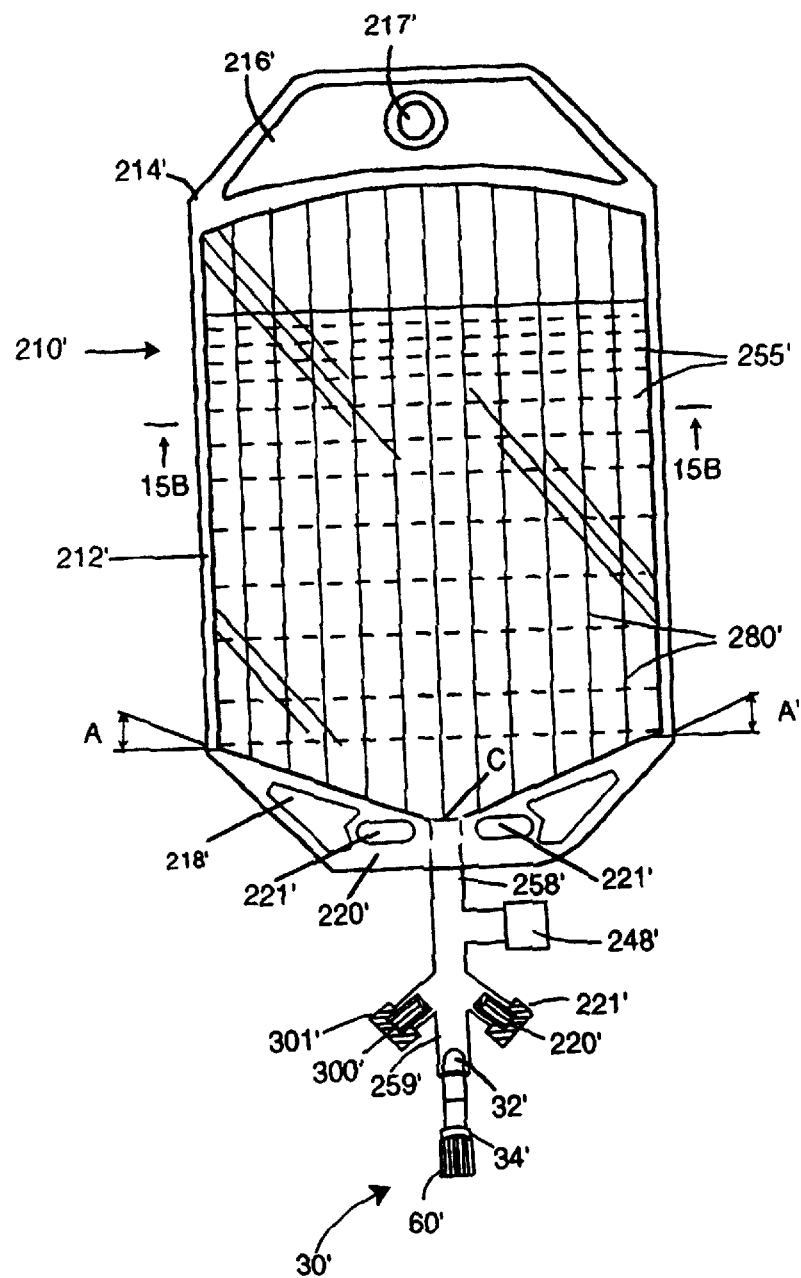
FIG. 15A is a plan view of the universal, flexible container multiple use universal connector assembly shown in FIG. 9 one wall of which is embossed with vertically oriented channels.
Figure 15B:
FIG. 15B is a cross-section of the universal, flexible container multiple use universal connector assembly shown in FIG. 15A taken along the line 15B—15B.
Figure 17A:
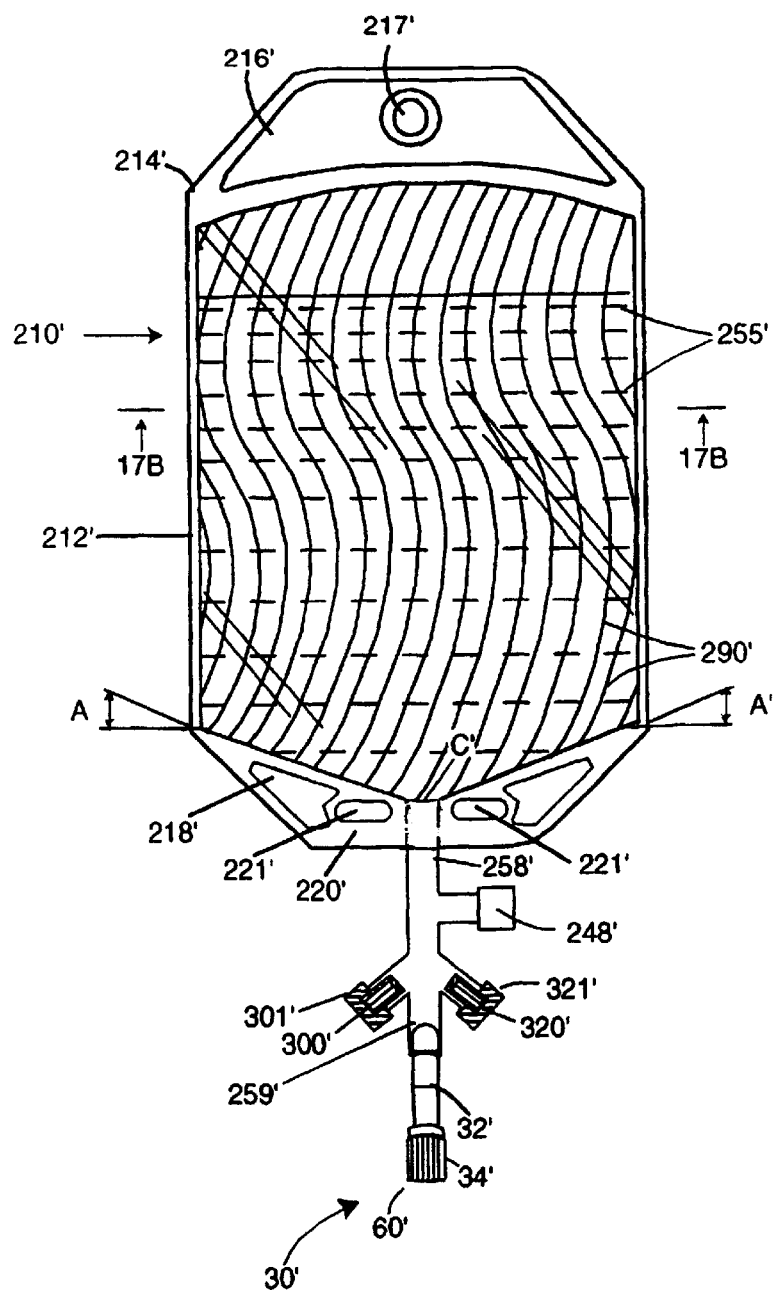
FIG. 17A is a plan view of the universal, flexible container multiple use universal connector assembly shown in FIG. 9A one wall of which is embossed with vertically oriented S-shape channels.
Figure 17B:
FIG. 17B is a cross-section of the universal, flexible container multiple use universal connector assembly shown in FIG. 17A taken along the line 17B—17B.

FIG. 15A and FIG. 15B show the embodiment described in FIG. 9, except that the inside wall of first sheet of pouch 210' is embossed 280' as described in FIGS. 14A and 14B.

Referring to FIG. 16A and FIG. 16B, the inside wall of first sheet of pouch 210 of FIG. 8 is embossed 290 with vertically oriented channels which have a slight S-shape configuration in a spaced relationship from each other. The size of the width of individual channels may be in the range of from about 0.01 to about 10 mms or larger. The channels may be spaced from each other of from about 10 microns to about 10 mms. While both inside walls of the first sheet and second sheet may be embossed, it is preferred that only one inside wall of the first or second sheet be embossed.

FIG. 10A and FIG. 10B show the embodiment described in FIG. 2, except that the inside wall of first sheet of pouch 10' is embossed 90' as described in FIGS. 9A and 9B.

Process of Making and Using the Container

The flexible plastic container in the form of a bag, pouch or bottle is made of two rectangular sheets of polymeric materials one of which is embossed and flat welded together on four sides so as to define between the two sheets and the four welded sides a reservoir. The volume of the container is zero before it is filled and typically has an internal volume capacity of from about 50 to about 5,000 ml when it is filled with a medical fluid, such as a parenteral solution.

Combination access member 258 or 258', needle access port 300 or 300', and spike access port 320 or 320' can be made by blow molding or other techniques known in the art.

Combination access member 258 or 258' are sealed between the superimposed sheets by the same welding process used to seal the superimposed sheets together. Upon completion of the welding process the container is suspended via holes 221 or 221', followed by filling the container through the access port IV with the desired fluid. Alternatively, the container may be sealed by heat welding at its four edges except at its bottom center portion C or C' and filled with the desired fluid prior to sealing combination access member 258 or 258' between the superimposed sheets. With either process, the universal, flexible container of the present invention, when it is filled with the desired fluid, provides for instant delivery via IV access port with the multiple use universal connector, needle or spike.

In the process of delivering the medical fluid to a patient using the IV access port equipped with the multiple use universal connector, the container 210 or 210' is suspended via hole 217 or 217', cap 60 or 60' is removed and a luer connector is engaged with multiple use universal connector. Vent 248' allows outside air to replace the drained medical fluid in the container so that fluid flow is steady and continuous. If fluid delivery is desired using the needle or spike access ports, the container is suspended via hole 217 or 217', caps 301 or 301' are removed and needle or spike is inserted into the respective ports to enable delivery of the medical fluid to the desired site on the patient.

In the second preferred embodiment, the present invention provides a universal, flexible plastic container, in the shape of a bag, pouch or bottle for the containment and delivery of diagnostic contrast media, nutrients and drug formulations.

Figure 18:
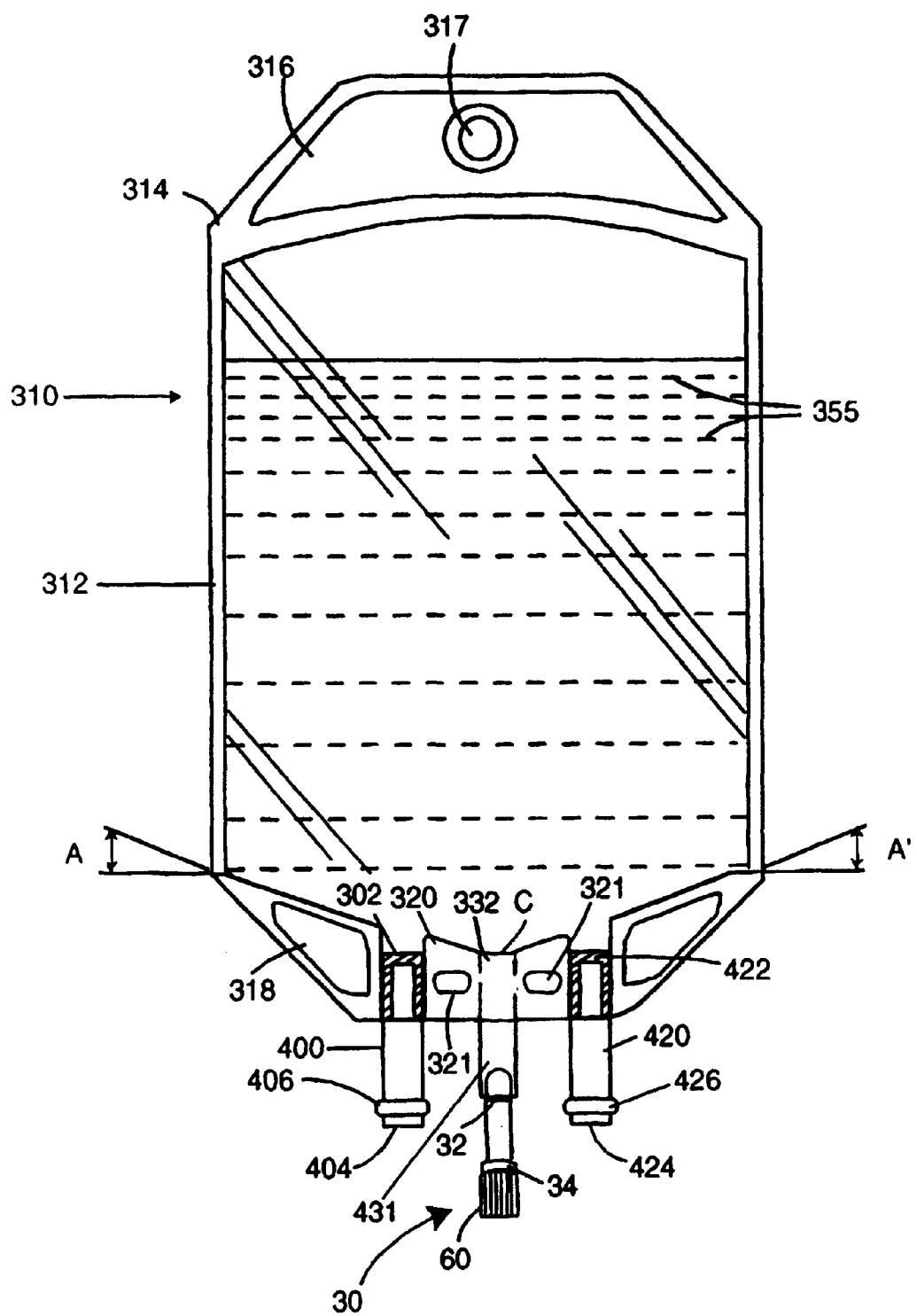
FIG. 18 is a plan view of a universal, flexible container multiple use universal connector assembly in accordance with the present invention showing:
a) a pouch with an IV access port located in the center, bottom portion of the pouch to which the multiple use universal connector is sealably attached;
b) a needle access port located in the bottom portion of the pouch on one side of the IV access port; and
c) a spike access port located in the bottom portion of the pouch on the other side of the IV access port.
Figure 19:
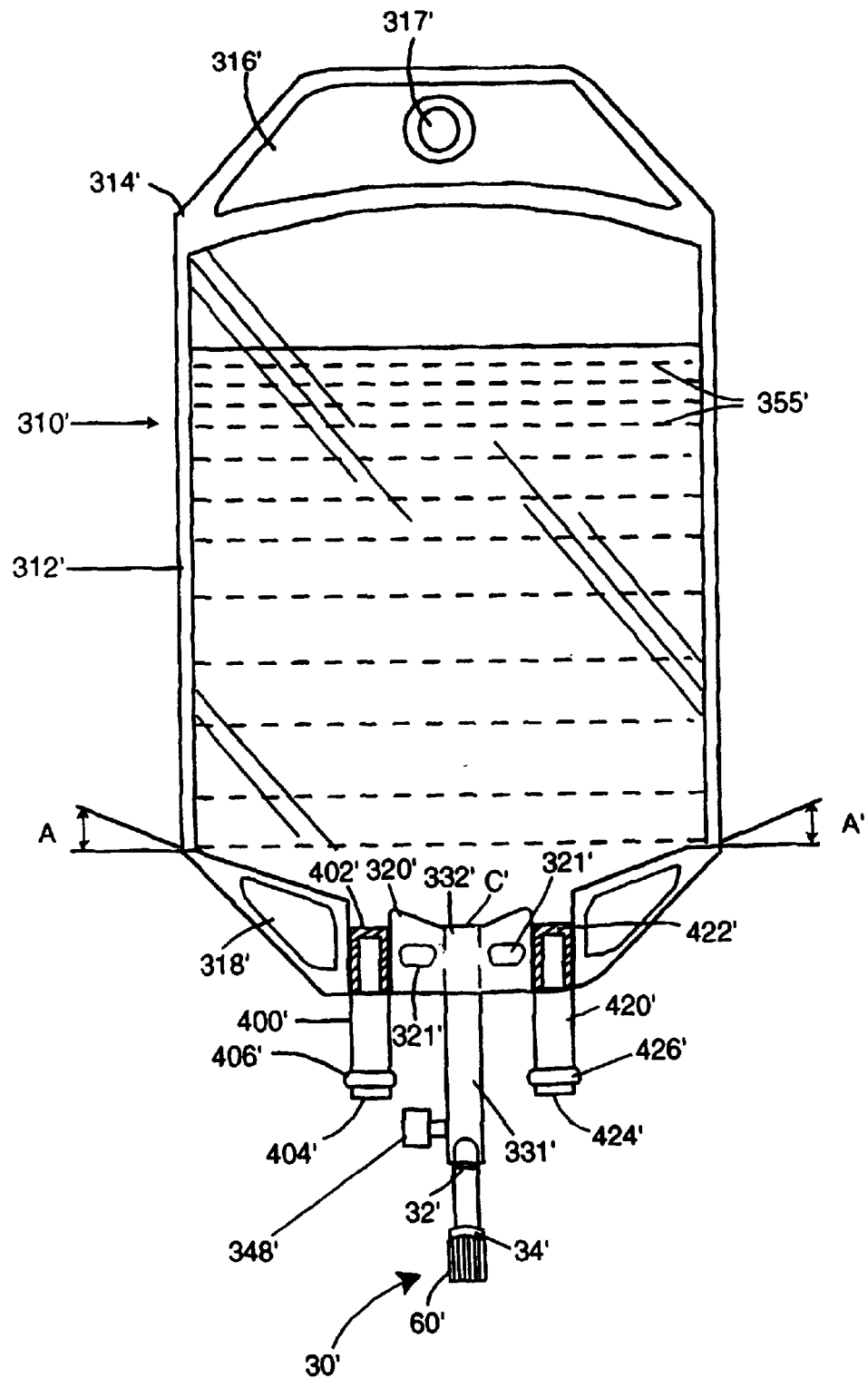
FIG. 19 is a plan view of another embodiment of the universal, flexible container in accordance with the present invention showing:
a) a pouch with an IV access port to which the multiple use universal connector is sealably attached, said IV access port is equipped with a vent;
b) a needle access port located in the bottom portion of the pouch on one side of the IV access port; and
c) a spike access port located in the bottom portion of the pouch on the other side of the IV access port.

In the drawings where like numerals indicate like elements or portions, the reference character 310 and 310' in FIGS. 18 and 19 indicate the container which, in a preferred embodiment, is a pouch-like device, comprising two superimposed sheets of suitable length and width made of flexible or pliable materials, such as polymeric materials including polyethylene, polypropylene, and preferably thermoplastic materials. The superimposed sheets forming the pouch-like container are preferably made of transparent materials so as to allow observation of the amount of its content during the filling operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably flat welded to each other so as to form the pouch whose volume is zero before it is filled with a parenteral solution. When the pouch is filled or partially filled as shown by 355 in FIG. 18 and 355' in FIG. 19, it assumes the shape of a small cushion. The superimposed sheets are joined together along marginal areas 312, 312', 314, 314', 316, 316', 318, 318', 320 and 320' as shown in FIGS. 18 and 19 respectively.

The bottom portion of pouch 310 or 310' terminates in first angle A and second angle A' from the center C or C' of said bottom portion and relative to a horizontal plane crossing the center C or C' of said bottom portion to direct and facilitate the flow of content contained in the pouch towards an IV access port 331 or 331', needle access port 400 or 400', and spike access port 420 or 420'. Angles A and A' are of from about 5° to about 45°, preferably from 10° to 30° and most preferably form 10 to 20°.

IV access port 331 or 331' located at center C or C' of the bottom portion of pouch 410 or 410' is sealed between the first sheet and second sheet of the pouch. Fixedly attached by heat sealing or other means, multiple use universal connector 30 or 30' is joined to IV access port 331 or 331'.

Marginal areas 316 and 316' in FIGS. 18 and 19 preferably comprise at least one hole 317 or 317' for suspending the pouch when it is in use for delivering the content of the pouch to a delivery site.

Marginal areas 320 and 320' in FIGS. 18 and 19 preferably comprise at least one, and more preferably a plurality, of hole(s) 321 and 321' to facilitate suspending the pouch during the filling process.

The IV access port may be configured with or without vent 348'.

Referring to FIGS. 18 and 19, on one side of the IV access port there is located needle access port 400 or 400', which is integral with pouch 310 or 310', sealed between the superimposed sheets at the time of manufacture of the pouch 310 or 310'. Needle access port 400 or 400', having proximal end 402 or 402' and distal end 404 or 404' is equipped at its distal end with crimp seal 406 or 406'. Access to the needle access port 400 or 400' using a steel needle is gained by severing crimp seal 406 or 406'.

On the other side of the IV access port there is located spike access port 420 or 420', which is also integral with pouch 410 or 410', sealed between the superimposed sheets at the time of manufacture of the pouch 400 or 400'. Spike access port 420 or 420', having proximal end 402 or 402', is equipped at its distal end with crimp seal 426 or 426'. Access to the spike access port 420 or 420', using a plastic spike, is gained by severing crimp seal 426 or 426'.

Needle access port 400 or 400' and spike access port 420 or 420' are positioned in the proximity of the IV access port, which positioning in combination with the bottom portion of pouch 310 or 310', having angle A or A', minimizes fluid waste/fluid hold up.

The container of the present invention may be used for delivering a single dose or multi-dose parenteral solution. The needle and spike ports, along with the IV access port equipped with the multiple use universal connector, allow access to the drug in the pouch by means that happen to be available under any circumstances.

In addition to providing multiple access ports, the present invention provides further improvement in flexible containers designed for delivering parenteral solutions, such as diagnostic contrast media and drug formulations.

It was discovered that if the inside wall of the first sheet or the second sheet forming the pouch 310 of FIG. 18 or pouch 310' of FIG. 19 is embossed, fluid hold up in the form of drops adhering to the inside walls can be reduced or eliminated and the walls, as the content of the pouch is being drained into the injection site, adhering together and further trapping drops of the fluid, can be prevented. In accordance with this discovery there are provided the following preferred embodiments of the invention.

Figure 20A:
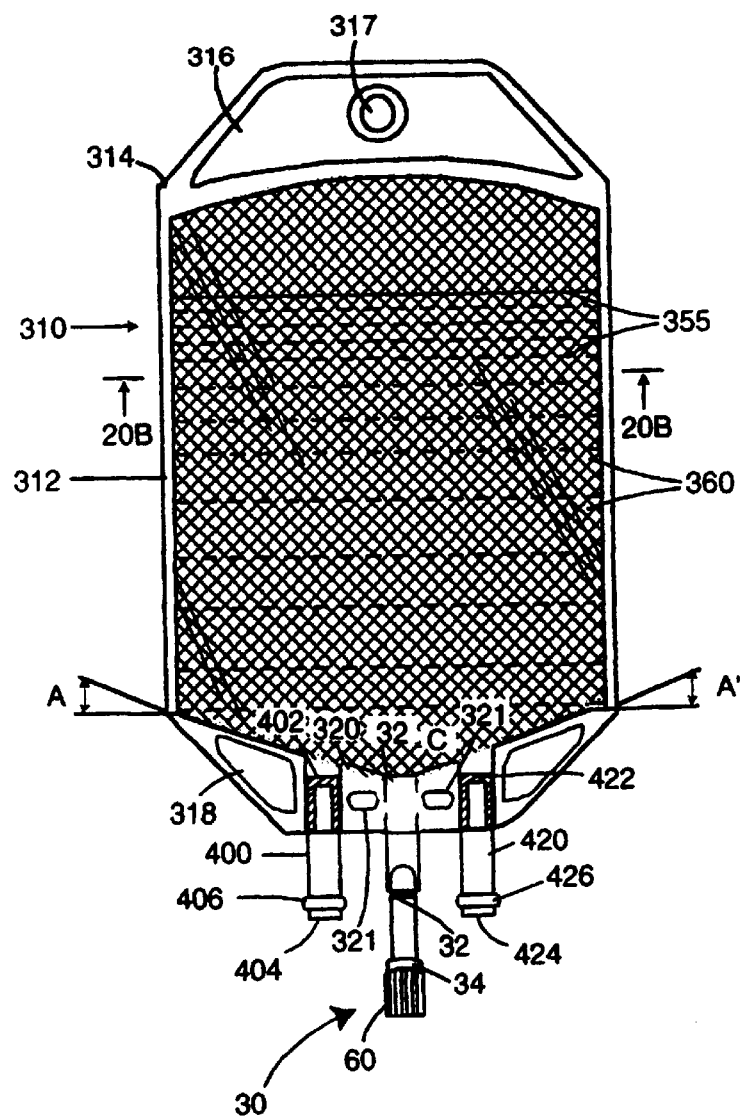
FIG. 20A is a plan view of the universal, flexible container multiple use universal connector assembly shown in FIG. 18 one wall of which is embossed in a checkerboard fashion.
Figure 20B:
FIG. 20B is a cross-section of the universal, flexible container multiple use universal connector assembly shown in FIG. 20A taken along the line 20B—20B.

Referring to FIG. 20A and FIG. 20B, the inside wall of first sheet of pouch 310 shown in FIG. 18 is embossed in a checkerboard manner 360, the checkerboard consisting of squares the 90° angles of which pointing downward towards the center C of the pouch. The size of the individual squares may be in the range of from 0.01 to 10 mm² or larger. The size of the individual squares may vary the determination of which would be influenced by the viscosity and the surface tension of the parenteral liquid for the delivery of which the pouch is intended.

While the inside wall of both first sheet and second sheet may be embossed, it was observed that the pouch functions better in terms of eliminating fluid hold up and preventing the superimposed walls from sticking together when only one inside wall of the first or second sheet is embossed.

Figure 21A:
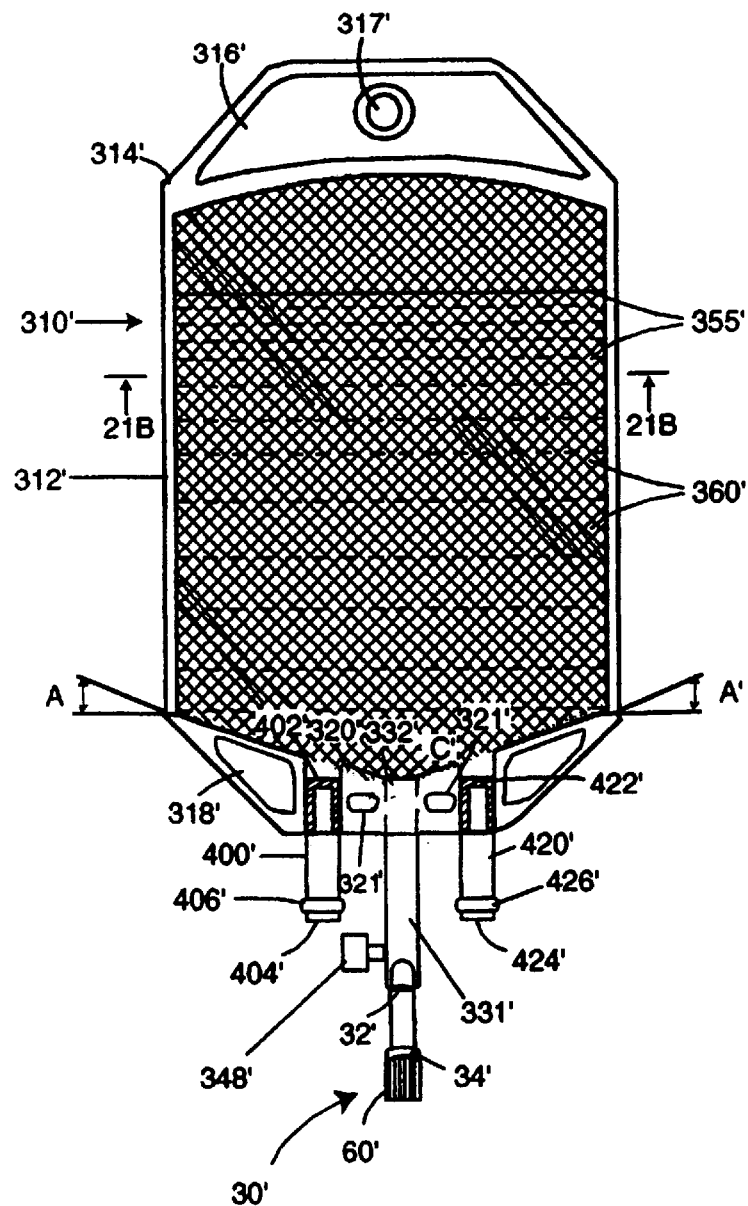
FIG. 21A is a plan view of the universal, flexible container multiple use universal connector assembly shown in FIG. 19 one wall of which is embossed in a checkerboard fashion.
Figure 21B:
FIG. 21B is a cross-section of the universal, flexible container multiple use universal connector assembly shown in FIG. 21A taken along the line 21B—21B.

FIG. 21A and FIG. 21B show the embodiment described in FIG. 19, except that the inside wall of first sheet of pouch 310' is embossed as described in FIG. 20A.

Figure 22A:
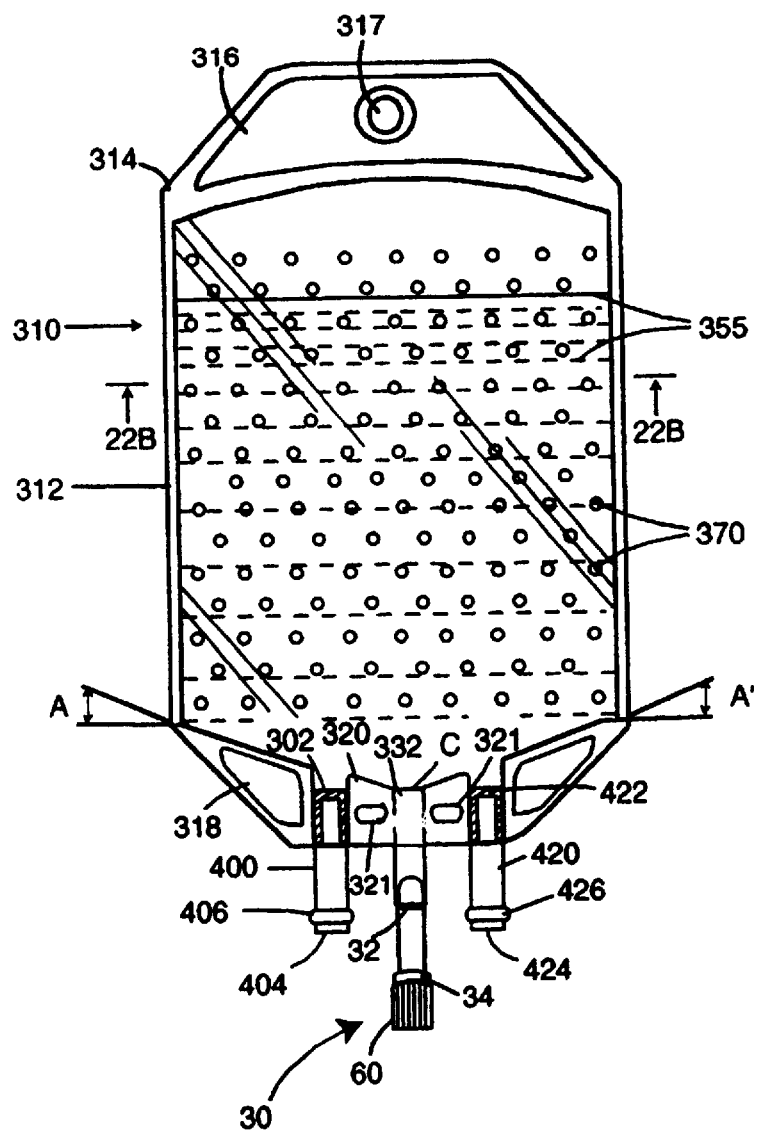
FIG. 22A is a plan view of the universal, flexible container multiple use universal connector assembly shown in FIG. 18 one wall of which is embossed in a dotted fashion.
Figure 22B:
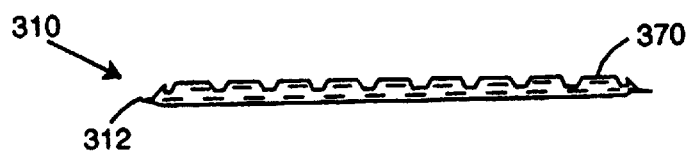
FIG. 22B is a cross-section of the universal, flexible container multiple use universal connector assembly shown in FIG. 22A taken along the line 22B—22B.

Referring to FIG. 22A and FIG. 22B, the inside wall of first sheet of pouch 310 of FIG. 18 is embossed with dots or micro circles 370 in a spaced relationship from each other. The dots or circles may vary in diameter from 5 microns to several mms and may be spaced from each other of from about10 microns to about 10 mms or longer. While both inside walls of the first sheet and second sheet may be embossed, it is preferred that only the first sheet or second sheet be embossed.

Figure 23A:
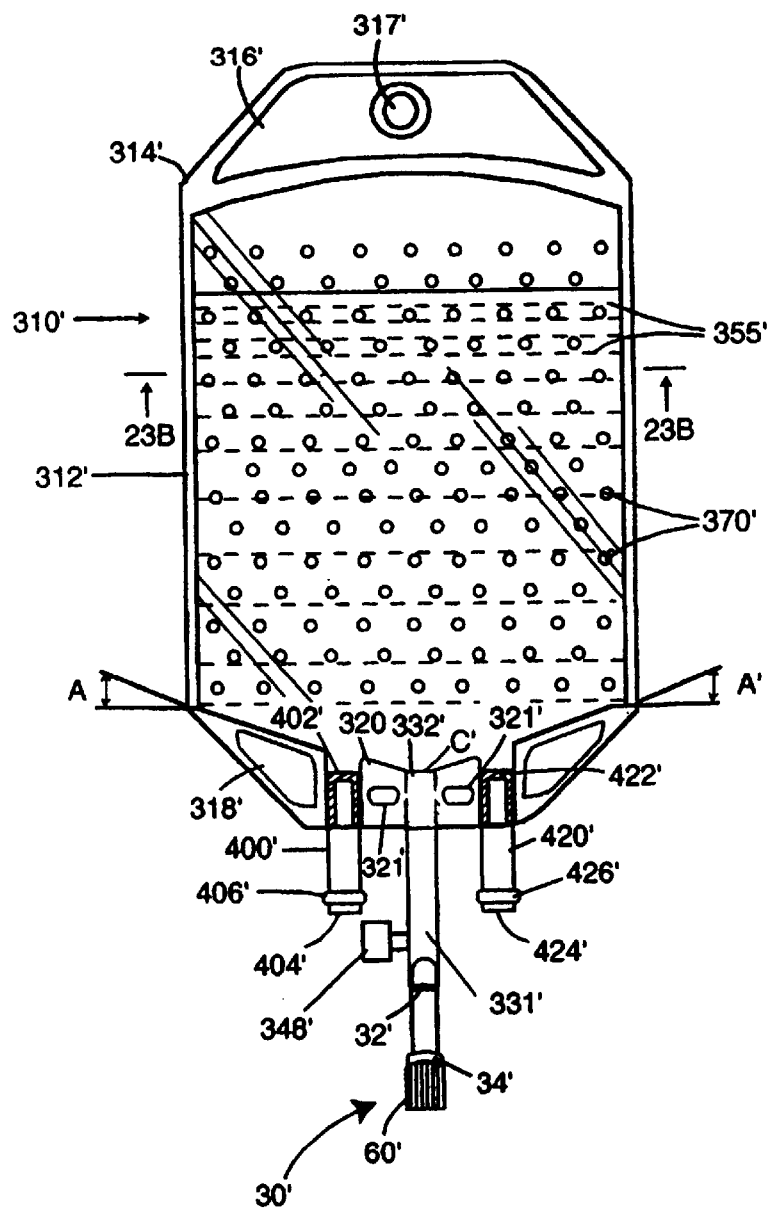
FIG. 23A is a plan view of the universal, flexible container multiple use universal connector assembly shown in FIG. 19 one wall of which is embossed in a dotted fashion.
Figure 23B:
FIG. 23B is a cross-section of the universal, flexible container multiple use universal connector assembly shown in FIG. 23A taken along the line 23B—23B.

FIG. 23A and FIG. 23B show the embodiment described in FIG. 19, except that the inside wall of first sheet of pouch 310' is embossed 370' as described in FIG. 22A.

Figure 24A:
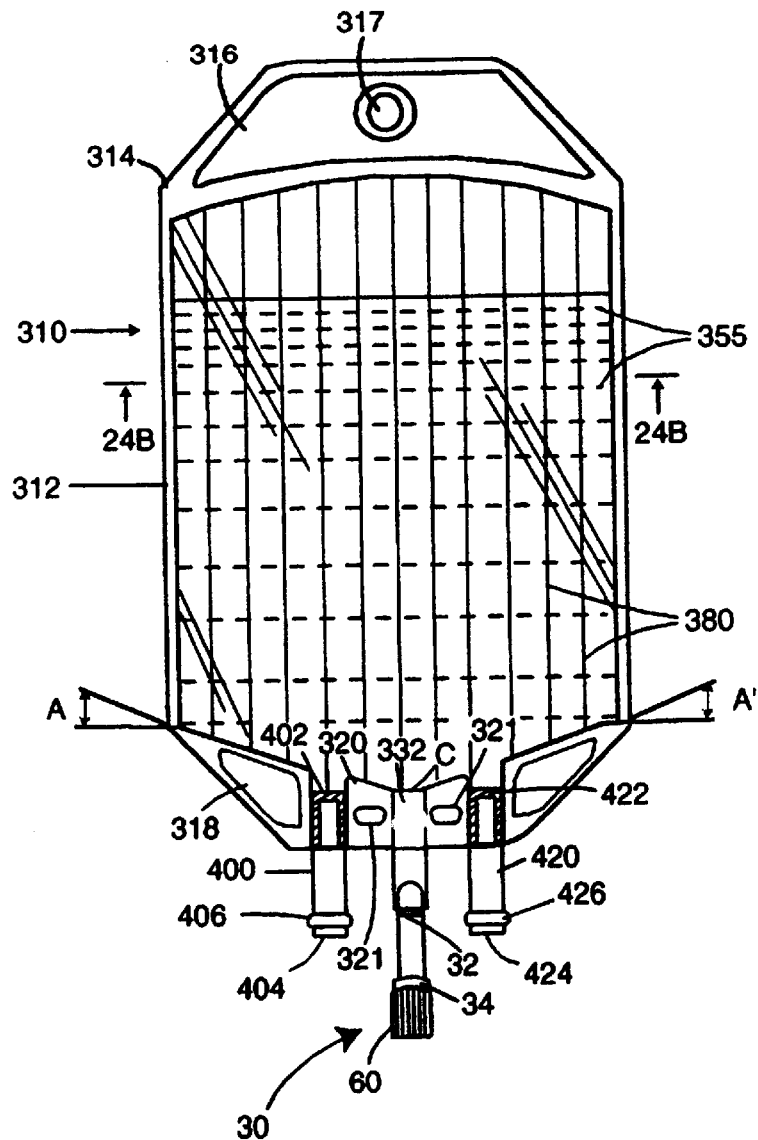
FIG. 24A is a plan view of the universal, flexible container multiple use universal connector assembly shown in FIG. 18 one wall of which is embossed with vertically oriented channels.
Figure 24B:
FIG. 24B is a cross-section of the universal, flexible container multiple use universal connector assembly shown in FIG. 24A taken along the line 24B—24B.

Referring to FIG. 24A and FIG. 24B, the inside wall of first sheet of pouch 310 shown in FIG. 18 is embossed 380 in vertical channel configuration in spaced relationship from each other. The width of the individual channels may be in the range of from about 0.01 to about 10 mm or larger. The channels may be spaced from each other of from about 10 microns to about 10 mms. While both inside walls of the first sheet and second sheet may be embossed, it is preferred that only one inside wall of the first or second sheet be embossed.

Figure 25A:
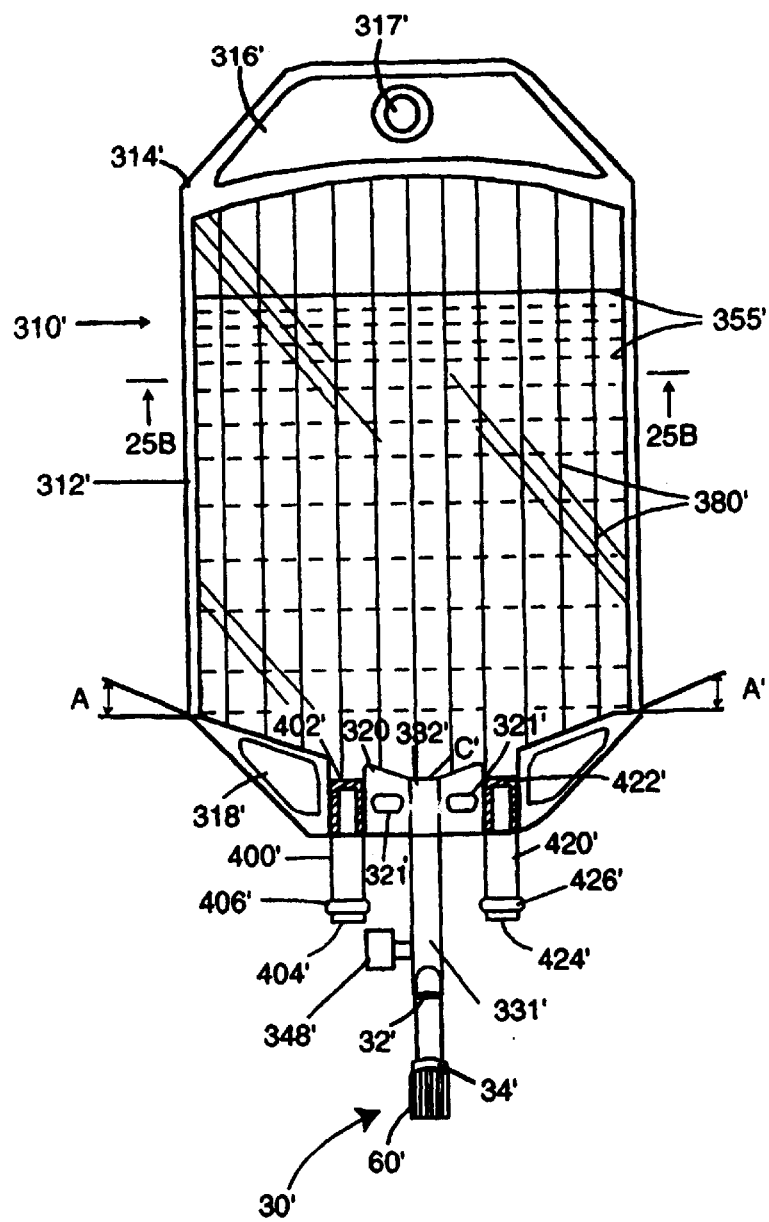
FIG. 25A is a plan view of the universal, flexible container multiple use universal connector assembly shown in FIG. 19 one wall of which is embossed with vertically oriented channels.
Figure 25B:
FIG. 25B is a cross-section of the universal, flexible container multiple use universal connector assembly shown in FIG. 25A taken along the line 25B—25B.

FIG. 25A and FIG. 25B show the embodiment described in FIG. 19, except that the inside wall of first sheet of pouch 310' is embossed 380' as described in FIG. 7A.

Figure 26A:
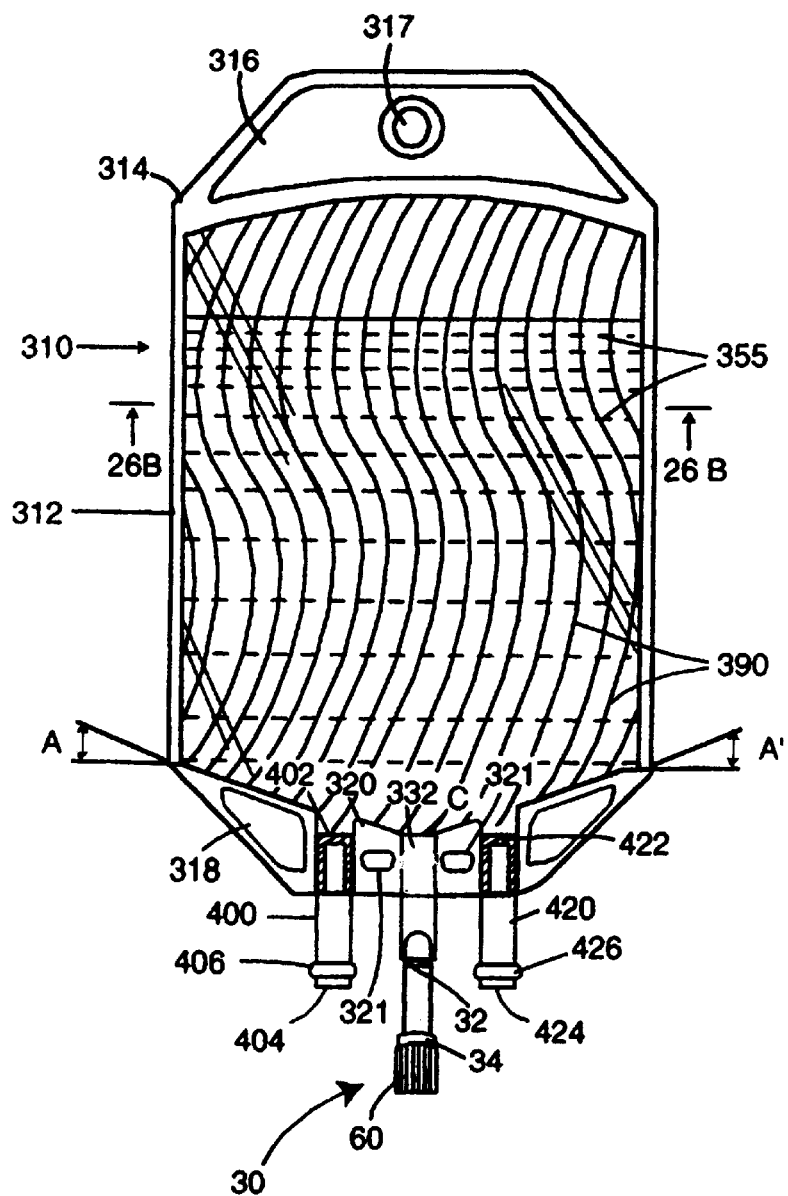
FIG. 26A is a plan view of the flexible container multiple use universal connector assembly shown in FIG. 19 one wall of which is embossed with vertically oriented S-shape channels.
Figure 26B:
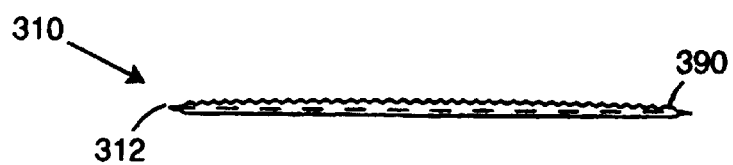
FIG. 26B is a cross-section of the universal, flexible container multiple use universal connector assembly shown in FIG. 26A taken along the line 29B—29B.

Referring to FIG. 26A and FIG. 26B, the inside wall of first sheet of pouch 310 of FIG. 18 is embossed 390 with vertically oriented channels which have a slight S-shape configuration in a spaced relationship from each other. The size of the width of individual channels may be in the range of from about 0.01 to about 10 mms or larger. The channels may be spaced from each other of from about 10 microns to about 10 mms. While both inside walls of the first sheet and second sheet may be embossed, it is preferred that only one inside wall of the first or second sheet be embossed.

Figure 27A:
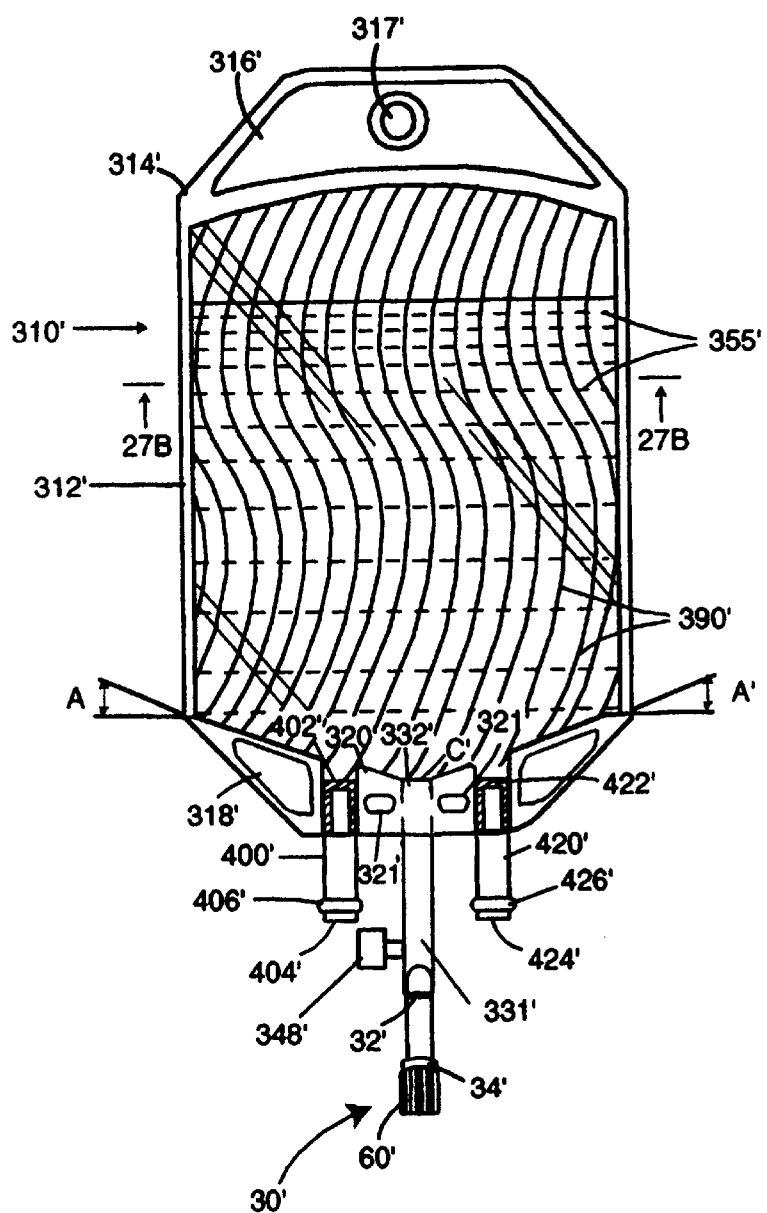
FIG. 27A is a plan view of the universal, flexible container multiple use universal connector assembly shown in FIG. 19 one wall of which is embossed with vertically oriented S-shape channels.
Figure 27B:
FIG. 27B is a cross-section of the universal, flexible container shown in FIG. 27A taken along the line 27B—27B.

FIG. 27A and FIG. 27B show the embodiment described in FIG. 19, except that the inside wall of first sheet of pouch 10' is embossed 90' as described in FIG. 26A.

Materials of Construction

The materials of construction is essentially the same as for the first embodiment of the present invention. The flexible container of the present invention is made of known polymeric materials having properties which make them suitable for sterile delivery of parenteral liquids. The sheets for forming the walls of the container are preferably multilayer sheets and characterized by heat resistance, gloss, strength, flexibility, and chemical inertness. Preferably the sheets are transparent or at least translucent enabling visual inspection of the contents at all times during delivery of content form the container to the patient. The container must be sterilizable, preferably by heat, along with its content. At least one layer of the sheet must be impervious to atmospheric gases and to steam. Preferably, the internal surface of the pouch in contact with the parenteral solution therein should be impervious to gas and steam. The interior layer in contact with the parenteral solution must not contain any toxic agents or even plasticizers which could leach out and contaminate the solution. The sheet may be made, for example, from polyvinylidene chloride sandwiched between two polyethylene or polyvinylacetate layers. The polyvinylidene chloride constitutes the impervious barrier. Further layers may be added to the face or back of the sheet, if desired, such as a polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm²; a moisture vapor transmission rate of about 14–20 (g/m²/day at 38° C., 100% RH); and an oxygen barrier of 650 (cc/m²/day at 23° C., 0% RH, bar. CRYOVAC® sterlizable medical films (W. R. Grace and Co.) are especially suitable to construct the sheets used in the present invention. The films comprise a polyethylene layer sandwiched between polyester outer layers sealed together by a modified propylene copolymer. Typical properties of the film include: a thickness of about 190 micron; a tensile strength of about 250 kg/cm²; a moisture vapor transmission rate of 5 (g/m²/day at 38° C., 100% RH); and an oxygen barrier of about 1500 (cc/m²/day at 23° C., 0% RH, bar).

Other polymeric films or sheets constructing the universal, flexible container of the present invention include: copolyester ether monolayer films, such as polycyclohexanedimethylcyclohexane, dicarboxylate elastomer made by Eastman Kodak Co.; and ethyl vinyl acetate made by Stedim, Inc. It is important that the fluid contacting layer of the multilayer sheet contain no plasticizer which may contaminate the fluid content of the container. Preferably, no plasticizer should be used at all on any of the multilayers to form the universal, flexible container of the present invention.

The sheets used in the present invention may be embossed with the described configuration by techniques known in the art. Alternatively, the layer constituting the internal liquid contacting layer of the sheet may be embossed prior to forming the multilayer sheets.

Access ports and tubing used in the present invention may be made of polyvinyl chloride which are sold commercially for use in medical devices. Other port and tubing materials may also be used, such as CRYOVAC® Port Tubing (W. R. Grace & Co.) which comprise three concentric layers of polymeric materials: a polyolefin layer is sandwiched between an outer layer of modified propylene copolymer and an inner layer of ethylene vinyl acetate or polyvinyl chloride.

Process of Making the Container

The flexible plastic container in the form of a bag, pouch or bottle is made of two rectangular sheets of polymeric materials one of which is embossed and flat welded together on four sides so as to define between the two sheets and the four welded sides a reservoir. The volume of the container is zero before it is filled and typically has an internal volume capacity of from about 50 to about 5,000 ml when it is filled with a medical fluid, such as a parenteral solution. Access ports 330 or 330', 402 or 402', and 422 or 422' are sealed by the same welding process used to seal the two superimposed layers of sheets together at the center C or C' of the container 310 or 310'. Upon completion of the welding process the container is suspended via holes 321 or 321', followed by filling the container through the IV access port equipped with the multiple use universal connector with the desired medical fluid.

In the process of delivering the medical fluid to a patient using the IV access port equipped with the multiple use universal connector, the container 310 or 310' is suspended via hole 317 or 317', cap 60 or 60' is removed and a luer connector or similar means is engaged with the IV access port. If fluid delivery is desired using the needle or spike access ports, the container is suspended via hole 17 or 17', crimp seal 106 or 126 is severed and needle or spike is inserted into the respective ports to enable delivery of the medical fluid to the desired site on the patient.

List of Reference Numbers Used

| Item | Number |
|---|---|
| Intravenous infusion bag (IV bag) | 10 |
| Fluid contained in bag | 12 |
| Fluid exit port or tube in IV bag | 14 |
| Distal end of fluid exit port or tube | 16 |
| Proximal end of fluid exit port or tube | 18 |
| Bottom seam of IV bag | 20 |
| Multiple use universal connector | 30,30' |
| Distal end of multiple use universal connector | 32,32' |
| Proximal end of multiple use universal connector | 34 |
| Inside wall of multiple use universal connector | 36 |
| Outside wall of multiple use universal connector | 38 |
| First cap-locking ring | 40,40' |
| Proximal end of second cap locking-ring | 41,41' |
| Second cap-locking ring | 42 |
| Distal end of inside wall of multiple use universal connector | 50 |
| Proximal end of inside wall of multiple use universal connector | 52,52' |
| Side wall of cylindrical opening at proximal end of multiple use universal connector | 54 |
| Bottom wall of cylindrical opening at proximal end of multiple use universal connector | 56 |
| Cylindrical cap of multiple use universal connector | 60,60' |
| Internal threads on cap | 66,66' |
| Bottom wall of cap | 68,68' |
| Top wall of cap | 70 |
| Plug | 71 |
| Central portion of top wall | 72 |
| Side wall of plug | 74 |
| Bottom wall of plug | 76 |
| Outside wall of cylindrical protuberance of cap | 78 |
| Bottom wall of cylindrical protuberance of cap | 80 |
| Shoulder connecting inside wall of cap and outside wall of cylindrical protuberance of cap | 82 |
| M-shaped diaphragm | 90,90' |
| Leg portion of M-shaped diaphragm | 92,92' |
| Cup-shaped portion of M-shaped diaphragm | 94,94' |
| Horizontal bottom portion of cup-shaped portion | 96 |
| Side portion of cup-shaped portion | 98,98' |
| Slit in bottom portion | 100,100' |
| Top surface of horizontal bottom portion | 102 |
| Bottom surface of horizontal bottom portion | 104 |
| Unpenetrated membrane | 106,106' |
| Luer connector | 120 |
| Cylindrical cap of luer connector | 130 |
| Top portion of cylindrical cap | 138 |
| Center top portion of cylindrical cap | 140 |
| Wall portion of cylindrical cap facing tubing conduit 150 | 144 |
| Tubing conduit in luer connector | 150 |
| Outside wall of tubing conduit | 152 |
| Inside wall of tubing conduit | 154 |
| Fluid channel | 156 |
| Bottom end portion of tubing conduit | 158 |
| First Preferred Embodiment | |
| Universal Connector | 30,30' |
| Distal end of universal connector | 32,32' |
| Proximal end of universal connector | 34,34' |
| Cap of universal connector | 60,60' |
| Pouch (formed by superimposed sheets) | 210,210' |
| Sealed marginal areas | 212,212',214,214' 216,216',218,218' 220,220' |
| Proximal end of access member - inverted Y shape configuration | 258,258' |
| Distal end of access member | 259,259' |
| Tines - needless access port | 300,300' |
| Tines - spike access port | 320,320' |
| Cap to cover spike access port | 301,301' |
| Cap to cover spike access port | 321,321' |
| Vent | 248,248' |
| Plurality of holes to suspend pouch during filling process | 221,221' |
| Plurality of holes to suspend pouch when delivering its content to a site | 217,217' |
| Checkerboard embossment | 260,260' |
| Dots or microcircles embossment | 270,270' |
| Vertical channel embossment | 280,280' |
| S-shape configuration embossment | 290,290' |
| Second Preferred Embodiment | |
| Pouch | 310,310' |
| Sealed marginal areas | 312,312',314,314' 316,316',318,318' 320,320' |
| Holes for suspending pouch when delivering content to a site | 317,317' |
| Holes for suspending pouch during the filling process | 321,321' |
| IV access port | 330,330' |

-continued

| | |
|---|---|
| Needle access port | 400,400' |
| Proximal end of needle access member | 402,402' |
| Distal end of access member | 404,404' |
| Crimp seal on needle access port | 406,406' |
| Spike access port | 420,420' |
| Proximal end of spike access port | 422,422' |
| Distal end of spike access port | 424,424' |
| Crimp seal on spike access port | 426,426' |
| Checkerboard embossment | 360,360' |
| Dots or microcircles embossment | 370,370' |
| Vertical channels embossment | 380,380' |
| S-shape configuration embossment | 390,390' |

Various modifications of the several embodiments disclosed will become apparent to those skilled in the art The invention is intended to include such modifications to be limited only by the scope of the claims.

What is claimed is:

1. A multiple use universal connector flexible medical container assembly for containment and delivery of a medical fluid comprising:
   a) a flexible medical container containing a medical fluid therein comprising first and second polymeric sheets having a square, round, oval, hexagonal, octagonal or rectangular configuration superimposed and sealed together at their periphery to form a pouch defining an interior reservoir having an inside wall, said pouch having a top portion and a bottom portion with a center therein; said bottom portion terminates in a first angle and a second angle of from about 5° to about 45° each from the center thereof and relative to a horizontal plane crossing the center of said bottom portion; portions of the inside wall of said interior reservoir being mechanically or chemically embossed;
   b) a combination access member of inverted Y shape configuration having:
      b1) a stem with a proximal end and a distal end, said proximal end located at the bottom, center portion of the pouch sealed between said first and second polymeric sheets; and
      b2) a pair of tines having proximal and distal ends, the proximal ends thereof being integral with the stem of the combination access member;
      the combination access member comprising:
   c) an IV access port at the distal end of the stem of the access member, equipped with a vent and a multiple use universal connector, said multiple use universal connector comprising:
      c1) a connector body of tube-like configuration having a distal end and a proximal end, wherein said proximal end is slideably inserted into the IV access port and said distal end is sealed by an elastomeric diaphragm and a removable cap;
      (c2) said elastomeric diaphragm is of M-shaped configuration, capable of flexing under pressure, and being capable of re-sealing itself after being pierced by an external access or transfer means; and
      (c3) said removable cap is threaded onto the distal end of said connector body to protect said elastomeric diaphragm from environmental forces and maintain said elastomeric diaphragm in aseptic condition prior to removal of said removable cap for accessing the medical fluid in said medical container or transferring a medical fluid into said flexible medical container by an access or a transfer means;
      (d1) a needle access port located in one of the tines of the combination access member; and
      (d2) a spike access port located in the other of the tines of the combination access member;
         said needle and spike access ports being equipped with caps.

2. The multiple use universal connector flexible medical container assembly of claim 1 wherein said connector body further comprises:
   (1) a first cap-locking ring on the proximal end of said connector body which serves as a male thread to receive said removable cap; and
   (2) a second cap-locking ring, spaced from said first cap-locking ring towards the distal end of said connector body, which serves as stopping means for the removable cap when the removable cap is threaded onto the connector body.

3. The multiple use universal connector flexible medical container assembly of claim 1 wherein said elastomeric diaphragm has a thickness of from about 5 mm to about 20 mm and a durometer of from about 25 to about 80 Shore A.

4. The multiple use universal connector flexible medical container assembly of claim 1 wherein said elastomeric diaphragm is of an elastomeric material selected from the group consisting of:
   natural rubber;
   acrylate-butadiene rubber;
   cis-polybutadiene;
   chlorobutyl rubber;
   chlorinated polyethylene elastomers;
   polyalkylene oxide polymers;
   ethylene vinyl acetate;
   fluorosilicone rubbers;
   hexafluoropropylene-vinylidene fluoride-tetrafluoroethylene terpolymers;
   butyl rubbers;
   polyisobutene;
   synthetic polyisoprene rubber;
   silicone rubbers,
   styrene-butadiene rubbers;
   tetrafluoroethylene propylene copolymers; and
   thermoplastic-copolyesters.

5. The multiple use universal connector flexible medical container assembly of claim 1 wherein said M-shaped elastomeric diaphragm comprises: a leg portion and a cup-shaped portion.

6. The multiple use universal connector flexible medical container assembly of claim 5 wherein said cup-shaped portion comprises: a horizontal bottom portion having a top surface and a bottom surface and a side portion which enclose an obtuse angle between them.

7. The multiple use universal connector flexible medical container assembly of claim 6 wherein said horizontal bottom portion comprises a slit extending from the top surface thereof toward the bottom surface thereof without penetrating said bottom surface.

8. The multiple use universal connector flexible medical container assembly of claim 6 wherein said cup-shaped portion comprises: a horizontal bottom portion and a side portion which enclose a semi-circular surface between them.

9. The multiple use universal connector flexible medical container assembly of claim 8 wherein said horizontal bottom portion comprises a slit extending from the top surface thereof toward the bottom surface thereof without penetrating said bottom surface.

10. The multiple use universal connector flexible medical container assembly of claim 1 wherein said elastomeric diaphragm reseals itself after puncture by an access or transfer means.

11. The multiple use universal connector flexible medical container assembly of claim 1 wherein said external access or transfer means comprises a luer connector or a syringe having a sharp or blunt needle cannula.

12. The multiple use universal connector flexible medical container assembly of claim 1 wherein said medical fluid is a therapeutic liquid.

13. The multiple use universal connector flexible medical container assembly of claim 1 wherein said medical fluid is diagnostic media.

14. The multiple use universal connector flexible medical container assembly of claim 1 wherein said medical fluid is a nutritional liquid.

15. The multiple use universal connector flexible medical container assembly of claim 1 wherein the inside wall of said interior reservoir is embossed in a checkerboard fashion.

16. The multiple use universal connector flexible medical container assembly of claim 1 wherein the inside wall of said interior reservoir is embossed with micro circles or dots.

17. The multiple use universal connector flexible medical container assembly of claim 16 wherein said micro circles or dots have a diameter of at least 5 microns and are spaced from each other of form about 10 microns to about 10 millimeters.

18. The multiple use universal connector flexible medical container assembly of claim 1 wherein the inside wall of said interior reservoir is embossed with vertical channels in spaced relationship from each other oriented in a length-wise direction of the flexible medical container.

19. The multiple use universal connector flexible medical container assembly of claim 18 wherein the width of each of said channels is of from about 0.01 and 10 millimeters and said channels are spaced from each other of from about 10 microns to about 10 millimeters.

20. The multiple use universal connector flexible medical container assembly of claim 1 wherein the inside wall of said interior reservoir is embossed with vertically oriented S-shaped channels in spaced relationship from each other oriented in a length-wise direction of the flexible medical container.

21. The multiple use universal connector flexible medical container assembly of claim 20 wherein the width of each of said S-shape channel is of from about 0.01 and 10 millimeters and said S-shaped channels are spaced from each other of from about 10 microns to about 10 millimeters.

22. The multiple use universal connector flexible medical container assembly of claim 1, wherein said first and second polymeric sheets are made of polyvinylidene chloride sandwiched between two layers of polyethylene or polyvinylacetate.

23. The multiple use universal connector flexible medical container of claim 1, wherein said first and second polymeric sheets are made of polyvinyl chloride.

24. The multiple use universal connector flexible medical container assembly of claim 1, wherein said first and second polymeric sheets are made of a polyethylene layer sandwiched between polyester outer layers sealed together by a propylene copolymer.

25. The multiple use universal connector flexible medical container assembly of claim 1, wherein said first and second polymeric sheets are made of polycyclohexanedimethylcyclohexane dicarboxylate.

26. The multiple use universal connector flexible medical container assembly of claim 1, wherein said first and second polymeric sheets are made of ethyl vinyl acetate.

27. A multiple use universal connector flexible medical container assembly with multiple access ports for the containment and delivery of a medical fluid comprising:
   a) a flexible medical container containing a medical fluid therein comprising first and second polymeric sheets having a square, round, oval, hexagonal, octagonal or rectangular configuration superimposed and sealed together at their periphery to form a pouch defining an interior reservoir having an inside wall, said pouch having a top portion and a bottom portion with a center therein;
      said bottom portion terminates in a first angle and a second angle of from about 50 to about 45° each from the center thereof and relative to a horizontal plane crossing the center of said bottom portion;
      portions of the inside wall of said interior reservoir being mechanically or chemically embossed;
   b) a first access member integral with said flexible medical container located at the center of said bottom portion allowing filling of the flexible medical container with a medical fluid and access thereto for delivery to a patient, said first access member comprising:
      an access port located below the bottom portion of said flexible medical container where said first angle and said second angle meet, said access port equipped with a vent and a multiple use universal connector, said multiple universal connector comprising:
      (b1) a connector body of tube-like configuration having a distal end and a proximal end, wherein said proximal end is slideably inserted into the access port and said distal end is sealed by an elastomeric diaphragm and a removable cap;
      (b2) said elastomeric diaphragm is of M-shaped configuration, capable of flexing under pressure, sealing said distal end of said connector body, and being capable of re-sealing itself after being pierced by an external access means; and
      (b3) a removable cap threaded onto the distal end of said connector body to protect said elastomeric diaphragm from environmental forces and maintain said elastomeric diaphragm in aseptic condition prior to removal of said removable cap;
   c) a second access member integral with said flexible medical container comprising a needle access port located on one side and adjacent to said first access member in the bottom portion of said container; and
   d) a third access member integral with said flexible medical container comprising a spike access port located on the other side and adjacent to said first access member in the bottom portion of said container, said needle and spike access ports being equipped with caps.

28. The multiple use universal connector flexible medical container assembly of claim 27 wherein said connector body further comprises:
   (3) a first cap-locking ring on the proximal end of said connector body which serves as a male thread to receive said removable cap; and
   (4) a second cap-locking ring, spaced from said first cap-locking ring towards the distal end of said connector body, which serves as stopping means for the removable cap when the removable cap is threaded onto the connector body.

29. The multiple use universal connector flexible medical container assembly of claim 27 wherein said elastomeric diaphragm has a thickness of from about 5 mm to about 20 mm and a durometer of from about 25 to about 80 Shore A.

30. The multiple use universal connector flexible medical container assembly of claim 27 wherein said elastomeric diaphragm is of an elastomeric material selected from the group consisting of:
- natural rubber;
- acrylate-butadiene rubber;
- cis-polybutadiene;
- chlorobutyl rubber;
- chlorinated polyethylene elastomers;
- polyalkylene oxide polymers;
- ethylene vinyl acetate;
- fluorosilicone rubbers;
- hexafluoropropylene-vinylidene fluoride-tetrafluoroethylene terpolymers;
- butyl rubbers;
- polyisobutene;
- synthetic polyisoprene rubber;
- silicone rubbers;
- styrene-butadiene rubbers;
- tetrafluoroethylene propylene copolymers; and
- thermoplastic-copolyesters.

31. The multiple use universal connector flexible medical container assembly of claim 27 wherein said elastomeric diaphragm reseals itself after puncture by an external transfer means.

32. The multiple use universal connector flexible medical container assembly of claim 27 wherein said external transfer means comprises a luer connector or a syringe having a sharp or blunt needle cannula.

33. The multiple use universal connector flexible medical container assembly of claim 27 wherein said medical fluid is a therapeutic liquid.

34. The multiple use universal connector flexible medical container assembly of claim 27 wherein said medical fluid is diagnostic media.

35. The multiple use universal connector flexible medical container assembly of claim 27 wherein said medical fluid is a nutritional liquid.

36. The multiple use universal connector flexible medical container of claim 27 wherein the inside wall of said interior reservoir is embossed in a checkerboard fashion.

37. The multiple use universal connector flexible medical container assembly of claim 27 wherein said M-shaped elastomeric diaphragm comprises: a leg portion and a cup-shaped portion.

38. The multiple use universal connector flexible medical container assembly of claim 37 wherein said cup-shaped portion comprises: a horizontal bottom portion having a top surface and a bottom surface and a side portion said horizontal bottom portion and said side portion enclose an obtuse angle between them.

39. The multiple use universal connector flexible medical container assembly of claim 38 wherein said horizontal bottom portion comprises a slit extending from the top surface thereof toward the bottom surface thereof without penetrating said bottom surface.

40. The multiple use universal connector flexible medical container assembly of claim 38 wherein said cup-shaped portion comprises: a horizontal bottom portion and a side portion which enclose a semi-circular surface between them.

41. The multiple use universal connector flexible medical container assembly of claim 40 wherein said horizontal bottom portion comprises a slit extending from the top surface thereof toward the bottom surface thereof without penetrating said bottom surface.

42. The multiple use universal connector flexible medical container assembly of claim 27 wherein the inside wall of said interior reservoir is embossed with micro circles or dots.

43. The multiple use universal connector flexible medical container assembly of claim 42 wherein said micro circles or dots have a diameter of at least 5 microns and are spaced from each other of from about 10 microns to about 10 millimeters.

44. The multiple use universal connector flexible medical container assembly of claim 27 wherein the inside wall of said interior reservoir is embossed with vertical channels in spaced relationship from each other oriented in a length-wise direction of the container.

45. The multiple use universal connector flexible medical container assembly of claim 44 wherein the width of each of said vertical channels is of from about 0.01 and 10 millimeters and said vertical channels are spaced from each other of from about 10 microns to about 10 millimeters.

46. The multiple use universal connector flexible medical container assembly of claim 27 wherein the inside wall of said interior reservoir is embossed with vertically oriented S-shaped channels in spaced relationship from each other and are oriented in a length-wise direction.

47. The multiple use universal connector flexible medical container assembly of claim 46 wherein the width of each of said S-shaped channels is of from about 0.01 and 10 millimeters, and said S-shaped channels are spaced from each other of from about 10 microns to about 10 millimeters.

48. The multiple use universal connector flexible medical container assembly of claim 27 wherein said first and second polymeric sheets are made of polyvinylidene chloride sandwiched between two layers of polyethylene or polyvinylacetate.

49. The multiple use universal connector flexible medical container assembly of claim 27 wherein said first and second polymeric sheets are made of polyvinyl chloride.

50. The multiple use universal connector flexible medical container assembly of claim 27 wherein said first and second polymeric sheets are made of polyethylene layer sandwiched between polyester outer layers sealed together by a propylene copolymer.

51. The multiple use universal connector flexible medical container assembly of claim 27 wherein said first and second polymeric sheets are made of polycyclohexanedimethylcyclohexane dicarboxylate.

* * * * *